United States Patent
Aebersold et al.

(10) Patent No.: US 7,364,911 B2
(45) Date of Patent: Apr. 29, 2008

(54) METHODS FOR ISOLATING AND LABELING SAMPLE MOLECULES

(76) Inventors: Rudolf H. Aebersold, 8609 SE. 78th St., Mercer Island, WA (US) 98040; Huilin Zhou, 13567 Foxglove Way, San Diego, CA (US) 92130; Beate Rist, Hinter den Gaerten 30, 31180Giesen (DE); George J. Vella, 2 Ledgewood Rd., Medway, MA (US) 02053; Subhasish Purkayastha, 49 Lexington Dr., Acton, MA (US) 01720; Sasi Pillai, 1 Nicole La., Littleton, MA (US) 01460

( * ) Notice: Subject to any disclaimer, the term of this patent is extended or adjusted under 35 U.S.C. 154(b) by 257 days.

(21) Appl. No.: 10/477,619

(22) PCT Filed: May 14, 2002

(86) PCT No.: PCT/US02/15500

§ 371 (c)(1),
(2), (4) Date: Jul. 12, 2004

(87) PCT Pub. No.: WO02/093131

PCT Pub. Date: Nov. 21, 2002

(65) Prior Publication Data

US 2004/0265810 A1    Dec. 30, 2004

(51) Int. Cl.
*G01N 24/00* (2006.01)
*G01N 21/76* (2006.01)
*G01N 33/68* (2006.01)
*G01N 33/92* (2006.01)

(52) U.S. Cl. .................. 436/86; 435/6; 436/71; 436/172; 436/173; 436/501; 530/402; 530/405

(58) Field of Classification Search .............. 435/6; 530/402, 405; 436/71, 173, 86, 501, 172
See application file for complete search history.

(56) References Cited

U.S. PATENT DOCUMENTS

| | | | |
|---|---|---|---|
| 6,057,096 A | 5/2000 | Rothschild et al. | |
| 2005/0233399 A1* | 10/2005 | Aebersold et al. ......... | 435/7.92 |

FOREIGN PATENT DOCUMENTS

| WO | WO 99/02728 | 1/1999 |
|---|---|---|
| WO | WO 00/11208 | 3/2000 |
| WO | WO 01/96869 | 12/2001 |
| WO | WO 02/48717 | 6/2002 |

OTHER PUBLICATIONS

Bodanszky and Bodanszky *The Practice of Peptide Synthesis*, vol. 21 Springer-Verlag, New York (1984), table of contents only.
Brancia et al., "A combination of chemical derivatisation and improved bioinformatic tools optimises protein identification for proteomics," *Electrophoresis* 22:552-559 (2001).
Glazer et al., "Laboratory Techniques in Biochemistry and Molecular Biology: Chemical Modification of Proteins," *Elsevier Biomedical Press*, New York Chapter 3, pp. 68-120 (1975).
Gygi et al., "Evaluation of two-dimensional gel electrophoresis-based proteome analysis technology," *Proc. Natl. Acad. Sci. USA* 97:9390-9395 (2000).
Gygi et al., "Quantitative analysis of complex protein mixtures using isotope-coded affinity tags," *Nature Biotechnol.* 17:994-999 (1999).
Houghten, R. "General method for the rapid solid-phase synthesis of large numbers of peptides: specificity of antigen-antibody interaction at the level of individual amino acides," *Proc. Natl. Acad. Sci. USA*, 82:5131-5135 (1985).
Hoving et al., "A method for the chemical generaton of N-terminal peptide sequence tags for rapid protein identification," *Anal. Chem.* 72:1006-1014 (2000).
Merrifield, R.B. "Solid Phase Peptide Synthesis," *J. Am. Chem. Soc.* 85:2149-2154 (1963).
Munchbach et al., "Quantitation and Facilitated de Novo Sequencing of Proteins by Isotopic N-Terminal Labeling of Peptides with a Fragmentation-Directing Moiety," *Anal. Chem.* 72:4047-4057 (2000).

(Continued)

*Primary Examiner*—Mary E. Ceperley
(74) *Attorney, Agent, or Firm*—McDermott Will & Emery LLP

(57) ABSTRACT

The invention provides methods for labeling a molecule by contacting a sample molecule with a solid support coupled to a chemical group comprising a cleavable functional group, one or more functional groups, and a reactive group for the sample molecule, under conditions allowing the sample molecule to covalently bind to the reactive group; and cleaving the cleavable functional group, thereby releasing the sample molecule comprising the one or more functional groups, which can be a tag. The invention also provides a solid support covalently coupled to a chemical group comprising a cleavable functional group, a mass spectrometry tag and a reactive group for covalently attaching a sample molecule, wherein the cleavable functional group, the tag and the reactive group are positioned relative to each other to allow transfer of the tag to the sample molecule upon cleavage of the cleavable functional group.

31 Claims, 16 Drawing Sheets

OTHER PUBLICATIONS

Wilson and Czarnik, eds., *Combinatorial Chemistry: Synthesis and Application*, John Wiley & Sons, New York (1997), table of contents only.

Zhou et al., "A systematic approach to the analysis of protein phosphorylation," *Nature Biotechnol.* 19:375-378 (2001).

Aebersold et al., "Mass spectrometry in proteomics," *Chem. Reviews* 101(2):269-295 (2001).

Geysen et al., "Isotope or mass encoding of combinatorial libraries," *Chem. Biol.* 3:679-688 (1996).

Zhou et al., "Quantitative proteome analysis by solid-phase isotope tagging and mass spectrometry," *Nature Biotech.* 19:512-515 (2002).

Aebersold and Goodlett, "Mass spectrometry in proteomics," *Chem. Reviews* 101: 269-295 (2001).

Bodanszky and Bodanszky, The practice of peptide synthesis, vol. 21 Springer-Verlag, New York (1984).

Geysen et al., "Istope or mass encoding of combinatorial libraries," *Chem. Biol.* 3:679-688 (1996).

Hoving et al., "A method for the chemical generation of N-terminal peptide sequence tags for rapid protein identification," *Anal. Chem.* 72:1006-1014 (2000).

Munchbach et al., "Quantitation and facilitated de novo seqencing of proteins by isotopic N-terminal labeling of peptides with a fragmentation-directing moiety," *Anal. Chem.* 72:4047-4057 (2000).

\* cited by examiner

METHODS FOR ISOLATING AND LABELING SAMPLE MOLECULES

BACKGROUND OF THE INVENTION

This invention was made with government support under grant number 1R33CA84698-0 awarded by the National Cancer Institute. The government has certain rights to the invention.

This invention relates generally to proteome analysis and more specifically to methods for transferring functional groups to molecules in a sample for analysis and quantitation of the molecules.

The classical biochemical approach to study biological processes has been based on the purification to homogeneity by sequential fractionation and assay cycles of the specific activities that constitute a process, the detailed structural, functional and regulatory analysis of each isolated component, and the reconstitution of the process from the isolated components. The Human Genome Project and other genome sequencing programs are turning out in rapid succession the complete genome sequences of specific species and, thus, in principle the amino acid sequence of every protein potentially encoded by that species. It is to be expected that this information resource unprecedented in the history of biology will enhance traditional research methods and catalyze progress in fundamentally different research paradigms, one of which is proteomics.

Efforts to sequence the entire human genome along with the genomes of a number of other species have been extraordinarily successful. The genomes of 46 microbial species (TIGR Microbial Database; www.tigr.org) have been completed and the genomes of over one hundred twenty other microbial species are in the process of being sequenced. Additionally, the more complex genomes of eukaryotes, in particular those of the genetically well characterized unicellular organism *Saccharomyces cerevisiae* and the multicellular species *Caenorhabditis elegans* and *Drosophila melanogaster* have been sequenced completely. Furthermore, "draft sequence" of the rice, human and *Arabidopsis* genomes have been published. Even in the absence of complete genomic sequences, rich DNA sequence databases have been made publicly available, including those containing over 2.1 million human and over 1.2 million murine expressed sequence tags (ESTs).

ESTs are stretches of approximately 300 to 500 contiguous nucleotides representing partial gene sequences that are being generated by systematic single pass sequencing of the clones in cDNA libraries. On the timescale of most biological processes, with the notable exception of evolution, the genomic DNA sequence can be viewed as static, and a genomic sequence database therefore represents an information resource akin to a library. Intensive efforts are underway to assign "function" to individual sequences in sequence databases. This is attempted by the computational analysis of linear sequence motifs or higher order structural motifs that indicate a statistically significant similarity of a sequence to a family of sequences with known function, or by other means such as comparison of homologous protein functions across species. Other methods have also been used to determine function of individual sequences, including experimental methods such as gene knockouts and suppression of gene expression using antisense nucleotide technology, which can be time consuming and in some cases still insufficient to allow assignment of a biological function to a polypeptide encoded by the sequence.

The proteome has been defined as the protein complement expressed by a genome. This somewhat restrictive definition implies a static nature of the proteome. In reality the proteome is highly dynamic since the types of expressed proteins, their abundance, state of modification, subcellular locations, and interactions with other biomolecules such as polypeptides and nucleic acids are dependent on the physiological state of the cell or tissue. Therefore, the proteome can reflect a cellular state or the external conditions encountered by a cell, and proteome analysis can be viewed as a genome-wide assay to differentiate and study cellular states and to determine the molecular mechanisms that control them. Considering that the proteome of a differentiated cell is estimated to consist of thousands to tens of thousands of different types of proteins, with an estimated dynamic range of expression of at least 5 orders of magnitude, the prospects for proteome analysis appear daunting. However, the availability of DNA databases listing the sequence of every potentially expressed protein combined with rapid advances in technologies capable of identifying the proteins that are actually expressed now make proteomics a realistic proposition. Mass spectrometry is one of the essential legs on which current proteomics technology stands.

Quantitative proteomics is the systematic analysis of all proteins expressed by a cell or tissue with respect to their quantity and identity. The proteins expressed in a cell, tissue, biological fluid or protein complex at a given time precisely define the state of the cell or tissue at that time. The quantitative and qualitative differences between protein profiles of the same cell type in different states can be used to understand the transitions between respective states. Traditionally, proteome analysis was performed using a combination of high resolution gel electrophoresis, in particular two-dimensional gel electrophoresis, to separate proteins and mass spectrometry to identify proteins. This approach is sequential and tedious, but more importantly is fundamentally limited in that biologically important classes of proteins are essentially undetectable (Gygi et al., *Proc. Natl. Acad. Sci. USA* 97:9390-9395 (2000).

The completion of the genomic sequence of a number of species has catalyzed a new approach to biology typically referred to as discovery science. The essence of discovery science is the systematic and quantitative analysis of all the members of a particular class of molecules expressed by a cell or tissue. Exemplary implementations of discovery science include the systematic analysis of mRNA molecules expressed by a cell or tissue by gene expression arrays and quantitative proteomics, the systematic analysis of the proteins contained in a biological sample. A main objective of discovery science is the description of the state of a cell or tissue (activity, pathology, stress) based on the data obtained from the systematic measurement of biomolecules and the identification of the molecular mechanisms that control the transition of a cell from one state to the other by the comparative analysis of the molecular composition of cells representing the two states. For the molecular description of a cellular state and mechanisms controlling it as many parameters as possible are desirable. Current expression array methods allow the systematic analysis of the mRNA molecules in a cell.

Recently, a method based on a class of reagents termed isotope coded affinity tags and mass spectrometry has been described that is suitable to systematically identify and quantify the proteins present in biological samples. Other properties relevant to the state of a cell, such as protein phosphorylation and other post translational modifications, and the quantitative profiles of biomolecules other than proteins or nucleic acids, for example, lipids, second messengers, metabolites, are difficult to measure systematically and quantitatively with current technology.

Thus, there exists a need for rapid, efficient, and cost effective methods for the analysis of molecules in a cell. The present invention satisfies this need and provides related advantages as well.

SUMMARY OF THE INVENTION

The invention provides methods for labeling a molecule by contacting a sample molecule with a solid support coupled to a chemical group comprising a cleavable functional group, one or more functional groups, and a reactive group for the sample molecule, under conditions allowing the sample molecule to covalently bind to the reactive group; and cleaving the cleavable functional group, thereby releasing the sample molecule comprising the one or more functional groups, which can be a tag. The invention also provides a solid support covalently coupled to a chemical group comprising a cleavable functional group, a mass spectrometry tag and a reactive group for covalently attaching a sample molecule, wherein the cleavable functional group, the tag and the reactive group are positioned relative to each other to allow transfer of the tag to the sample molecule upon cleavage of the cleavable functional group.

BRIEF DESCRIPTION OF THE DRAWINGS

FIG. 1 shows a schematic diagram of a solid phase based approach to capture polypeptides via a photo-cleavable linker that allows light captured recovery of the polypeptides.

FIG. 2 shows liquid chromatography-mass spectrometry (LC-MS) analysis of the peptide laminin B following reduction with tris(2-carboxyethyl)phosphine (TCEP) and the control peptide phosphoangiotensin.

FIG. 3 shows LC-MS of a mixture of reduced laminin B and phosphoangiotensin following contact with beads as shown in FIG. 1.

FIG. 4 shows LC-MS analysis of laminin B photo-cleaved from beads as treated in FIG. 3.

FIG. 6 shows LC-MS analysis of phosphoangiotensin modified with SATA.

FIG. 7 shows LC-MS analysis of SATA treated phosphoangiotensin further treated with hydroxylamine and reduction with TCEP, as shown in FIG. 5.

FIG. 9A shows the number of proteins identified from large-scale experiment (L), in which 100 μg total protein sample was labeled and 20 μg was analyzed by μLC-MS/MS. The solid-phase method quantified 82 proteins, and 33 proteins were quantified by the ICAT method, with 25 proteins in common. FIG. 9B shows the number of proteins identified from small-scale experiment (S), in which 10 μg of total sample was labeled and 5 μg analyzed. The solid-phase quantified 57 proteins, and 18 proteins were quantified by the ICAT method, with 13 proteins in common. FIG. 9C shows the number of proteins identified by the solid-phase method in large-scale (L) and small-scale (S) experiment. Numbers in segments of Venn diagrams indicate the number of proteins quantified.

DETAILED DESCRIPTION OF THE INVENTION

Figure 1A:
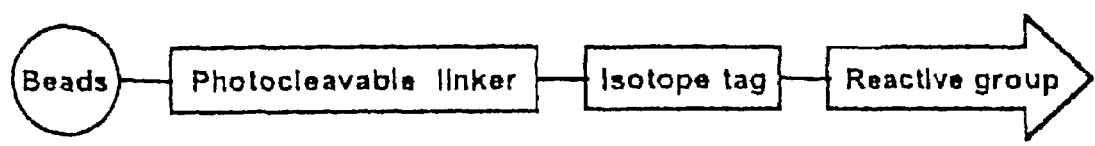
FIG. 1A shows a schematic representation of a solid-phase isotope tagging reagent with four elements: beads, photocleavable linker, stable isotope tag, and specific reactive group.

The invention provides methods and compositions for labeling molecules in a sample by capturing the molecules on a solid support with a chemical group that allows transfer of desirable functional groups, including tags useful for enhanced detection and to facilitate identification and quantitation of tagged molecules, to the molecules. The methods are advantageous in that they can be used to selectively isolate and label molecules from a sample, allowing quantitative analysis of complex mixtures of analytes, including analysis by methods such as mass spectrometry. Thus, the methods can be used to isolate essentially all of a particular class of molecules or a subset of molecules, for example, essentially all polypeptides or the subset of phosphoproteins, glycoproteins, or otherwise modified polypeptides.

Using general covalent capture-and-release chemistries, specific functional groups can be transferred to the components of a complex sample. Furthermore, by incorporating the ability to release a captured molecule, the methods can also advantageously be used to isolate or purify sample molecules, which can be useful for reducing the complexity of a sample being analyzed. The methods are well suited for quantitative proteome analysis, for the systematic and quantitative analysis of protein phosphorylation and other post translational modifications and can be extended to the systematic and quantitative analysis of molecules other than proteins and peptides. Moreover, the methods of the invention are advantageous in that sample molecules can be efficiently captured and released, allowing the use of smaller amounts of starting sample, which is particularly useful for analyzing complex biological samples for proteomics analysis.

The methods of the invention are particularly useful for identification and quantitative analysis of the molecules contained in biological samples, in particular the analysis of proteins for quantitative proteomics. The methods can also be used for the systematic, quantitative analysis of protein phosphorylation or other modifications on otherwise modified proteins. The invention also provides reagents that are useful for labeling molecules. In addition to proteomics analysis, the methods are also useful for the systematic and quantitative analysis of other biomolecules in addition to proteins. The methods are particularly useful for transferring labels or tags to molecules suitable for mass spectrometry (MS) analysis.

As used herein, the term "polypeptide" refers to a peptide or polypeptide of two or more amino acids. A polypeptide, can also be modified by naturally occurring modifications such as post-translational modifications or synthetic modifications, including phosphorylation, lipidation, prenylation, palmitylation, myristylation, sulfation, hydroxylation, acetylation, glycosylation, ubiquitination, addition of prosthetic groups or cofactors, formation of disulfide bonds, proteolysis, assembly into macromolecular complexes, and the like.

A polypeptide includes small polypeptides having a few or several amino acids as well as large polypeptides having several hundred or more amino acids. Usually, the covalent bond between the two or more amino acid residues is an amide bond. However, the amino acids can be joined together by various other means known to those skilled in the peptide and chemical arts. Therefore, the term polypeptide is intended to include molecules which contain, in whole or in part, non-amide linkages between amino acids, amino acid analogs, and mimetics. Similarly, the term also includes cyclic polypeptides and other conformationally constrained structures.

A modification of a polypeptide, particularly ligand polypeptides, can also include non-naturally occurring derivatives, analogues and functional mimetics thereof generated by chemical synthesis, provided that such polypeptide modification displays a similar functional activity compared to the parent polypeptide. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those polypeptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds.

A particularly useful polypeptide derivative includes modification to incorporate desirable functional characteristics using the methods disclosed herein. Such modifications include the incorporation of a label or tag, particularly labels or tags useful for MS analysis.

As used herein, the term "nucleic acid" when used in reference to a component of a biochemical system, is intended to mean two or more nucleotides covalently bonded together such as deoxyribonucleic acid (DNA) or ribonucleic acids (RNA) and including, for example, single-stranded and a double-stranded nucleic acid. The term is similarly intended to include, for example, genomic DNA, cDNA, mRNA and synthetic oligonucleotides corresponding thereto which can represent the sense strand, the antisense strand or both.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics lysine (Lys or K) would have a positive charge moiety located in similar molecular space and having the same degree of mobility as the ε-amino group of the side chain of the naturally occurring Lys amino acid. Mimetics also include constrained structures so as to maintain optimal spacing and charge interactions of the amino acid or of the amino acid functional groups.

As used herein, a "functional group" refers to a chemical group that has desirable functional properties. A desirable functional property is any property that imparts a desirable chemical characteristic to a molecule. A functional group can include a group that changes the physicochemical properties of a molecule, for example, changing the mass, charge, hydrophobicity, and the like. A particularly useful functional group is a label or tag, for example, fluorophores, chromophores, spin labels, isotope distribution tags, and the like.

As used herein, the term "label" is intended to mean any moiety that can be attached to a molecule that results in a change in mass of that molecule. The label can be bound to the molecule either covalently or non-covalently, although generally the label will be covalently bound. It is understood that, where a non-covalent interaction occurs between the label and the molecule, the non-covalent interactions are of sufficiently high affinity to allow the label to remain bound to the molecule during chemical and/or physical manipulations used in methods of the invention.

A particularly useful label is a mass label useful for analysis of a sample by MS. The change in mass of the molecule due to the incorporation of a mass label should be within the sensitivity range of the instrument selected for mass determination. In addition, one skilled in the art will know or can determine the appropriate mass of a label for molecules of different sizes and different compositions. Moreover, when using heavy and light mass labels, for example, for differential labeling of molecules, a mass difference as small as between about 1-3 mass units can be used or as large as greater than about 10 mass units, for example, about 4, about 5, about 6, about 7, about 8, about 9, about 10, about 12, about 15, or about 20 mass units or greater, as desired. Mass labels suitable for differentially labeling two samples are chemically identical but differ in mass.

As used herein, a "tag" refers to a label that is detectable. The tag imparts a characteristic to a molecule such that it can be detected by any of a variety of analytical methods, including MS, chromatography, fluorography, spectrophotometry, immunological techniques, and the like. A tag can be, for example, an isotope, fluor, chromagen, ferromagnetic substance, luminescent tag, or an epitope tag recognized by an antibody or antibody fragment. A particularly useful tag is a mass tag, which is a mass label suitable for detection and analysis of a molecule by MS. Exemplary mass tags include, for example, a stable isotope tag, an isotope distribution tag, a charged amino acid, differentially isotopically labeled tags, and the like. A tag can also be a gas-phase basic group such as pyridyl or a hydrophobic group. A tag can also be an element having a characteristic isotope distribution, for example, chlorine, bromine, or any elements having distinguishable isotopic distribution. Additionally, a tag can have a bond that breaks in a collision cell or ion source of a mass spectrometer under appropriate conditions and produces a reporter ion.

A tag can also be an affinity tag that allows isolation of a molecule coupled to the affinity reagent by binding to a cognate binding partner of the affinity tag. For polypeptide tagging, a polypeptide or polypeptides in a sample can be denatured, optionally reduced, and a chemically reactive group of the polypeptide covalently derivatized with a chemical modification reagent. Tagged polypeptides can be easily isolated from untagged polypeptides and other components within a sample, which reduces the complexity of the sample that is to be analyzed by mass spectrometry. Such affinity tagging can similarly be applied to other molecules such as nucleic acids, lipids, carbohydrate, second messengers, metabolites, and the like. Furthermore, a tag can be introduced by a chemical or enzymatically catalyzed reaction.

As used herein, a "cleavable functional group" is a chemical group that can be cleaved by a variety of methods, including input of energy, a chemical, an enzyme, and the like. For use in methods of the invention, the cleavable functional group is generally specific, that is, one which can be specifically cleaved without altering or damaging the molecule being cleaved or which relatively uniformly alters the molecule in a reproducible manner. For example, the cleavable functional group can be a photo-cleavable group. In such a case, the photo-cleavable group is generally cleaved at a wavelength of light that does not damage the molecule being released, for example, in the ultraviolet to visible range (see Example I). Exemplary photocleavable linkers include, for example, linkers containing o-nitrobenzyl, desyl, trans-o-cinnamoyl, m-nitrophenyl, benzylsulfonyl groups and the like (see, for example, Dorman and Prestwich, *Trens Biotech.* 18:64-77 (2000); Greene and Wuts, *Protective Groups in Organic Synthesis*, 2nd ed., John Wiley & Sons, New York (1991); U.S. Pat. Nos. 5,143,854; 5,986,076; 5,917,016; 5,489,678; 5,405,783).

The cleavable functional group can also be a chemical cleavable group cleavable by a chemical such as an acid or base. If desired, a chemical cleavage reaction can be carried out under relatively mild conditions in which the chemical cleavable group is essentially the only chemical bond cleaved. A chemical cleavable group can also be a group cleavable by a chemical such as CNBr, which can cleave a methionine residue. CNBr can be particularly useful for releasing a molecule if a chemical cleavable group such as methionine has been added to the molecule, particularly in a polypeptide that does not have a methionine residue. Suitable chemical cleavable groups are well known to those skilled in the art (see, for example Wilson and Czarnik, eds., *Combinatorial Chemistry: Synthesis and Application*, John Wiley & Sons, New York (1997); Merrifield, *J. Am. Chem. Soc.* 85:2149 (1964); Bodanszky, M., *Principles of Peptide Synthesis* (Springer-Verlag, 1984); Houghten, *Proc. Natl. Acad. Sci., USA* 82:5131 (1985)). Exemplary chemical cleavable linkers can contain a disulfide, which can be cleaved with reducing agents; a diol, which can be cleaved with periodate; a diazo bond, which can be cleaved with dithionate; an ester, which can be cleaved with hydroxylamine; a sulfone, which can be cleaved with base, and the like (see Hermanson, *Bioconjugate Techniques*, Academic Press, San Diego (1996); Pierce Chemical Co., Rockford Ill.).

The cleavable functional group can also be an enzymatic cleavable group. For example, a protease can be used to cleave a cleavable functional group having a suitable recognition sequence for the protease. Particularly useful proteases are endopeptidases such as factor Xa, tobacco etch virus (TEV) protease, trypsin, chymotrypsin, *Staphylococcus aureus* protease, submaxillaris protease, and the like. The protease can be selected based on the incorporation of a particular cleavable recognition sequence as a functional group. Other considerations for selecting a protease include the presence or absence of a recognition sequence in the molecule being captured and released.

For example, a rare cleaving protease such as TEV protease or factor Xa can be used to cleave a functional group containing the corresponding protease recognition sequence, resulting in release of the captured molecule. Such rare cleaving proteases are particularly useful for releasing an intact polypeptide molecule since the recognition sequence for these proteases would not occur in the vast majority of polypeptides. Alternatively, a polypeptide sample can be treated with a specific protease, and the digested peptides isolated by the methods disclosed herein. In such a case, the captured peptides would not contain a recognition sequence for the protease used for cleavage since the polypeptide has already been digested. In addition, if desired, an intact polypeptide can be captured and digested with a protease after binding to the solid support, resulting in the incorporation and release of a label on the peptide fragment of the polypeptide that was captured on the solid support. Thus, protease digestion can be used before or after capture of a sample molecule, in particular polypeptide sample molecules, as desired.

In addition to proteases, a cleavable functional group can be a recognition sequence for an endonuclease such as a restriction enzyme. Thus, an appropriate recognition sequence for a restriction enzyme can be incorporated as a cleavable functional group and cleaved with the respective restriction enzyme. It is understood that such a nucleotide functional group can be useful for capturing and releasing a nucleic acid or a polypeptide, or any other type of molecule, as desired. Similarly, a protease recognition sequence can be useful for capturing and releasing a polypeptide, nucleic acid or any other type of molecule, as desired.

As used herein, the term "reactive group" is intended to mean any of a variety of chemical groups having useful chemical properties suitable for reacting and covalently binding to a molecule such as a polypeptide, nucleic acid, lipid, carbohydrate, a second messenger, a metabolite, and the like. For example, a reactive group can react with carboxyl groups found in Asp or Glu, or the reactive group can react with other amino acids such as His, Tyr, Arg, and Met. A reactive group can also react with amines such as Lys, for example, imidoesters and N-hydroxysuccinimidyl esters. In addition, a reactive group can also react with oxygen or sulfur using chemistry well known in the art. A reactive group can also react with a phosphate group for selective labeling of phosphopeptides or nucleic acids, or with other covalently modified peptides, including glycopeptides, lipopeptides, or any of the covalent polypeptide modifications, such as those disclosed. herein.

As used herein, the term "isotopic label" or "isotope tag" refers to a chemical group which can be generated in two distinct isotopic forms, for example, heavy and light isotopic versions of the constituent elements making up the chemical group. Such constituent elements include, for example, carbon, oxygen, hydrogen, nitrogen, and sulfur. In addition, other elements that are chemically or functionally similar can be substituted for the above naturally occurring elements. For example, selenium can be used as a substitute for sulfur. Particularly useful isotopic labels or tags are those that allow convenient analysis by MS. For example, heavy and light isotopic versions of an amino acid can be used to differentially isotopically label a polypeptide (see Example I).

As used herein, "coupled," or grammatical forms thereof, refers to the binding interaction between molecules. For example, a solid support can be coupled to a chemical group via binding interactions between a chemical moiety of the solid support and a chemical moiety of the chemical group. The binding interaction between coupled molecules can be covalent or non-covalent. Generally, a chemical group is coupled to a solid support or other molecule via covalent interactions. It is understood that, where a non-covalent interaction occurs between the solid support and coupled molecules, the non-covalent interactions are of sufficiently high affinity to remain bound during chemical and/or physical manipulations used in methods of the invention, for example, chemical modification or washing steps carried out on molecules bound to the solid support.

The invention provides a method for labeling a molecule by contacting a sample molecule with a solid support coupled to a chemical group comprising a cleavable functional group, one or more functional groups, and a reactive group for the sample molecule, under conditions allowing the sample molecule to covalently bind to the reactive group. The method can further include the step of cleaving the cleavable functional group, thereby releasing the sample molecule having one or more functional groups attached. The methods are advantageous in that a molecule in a complex sample mixture can be captured and labeled for convenient analysis and, due to the ability to be released from the solid support, can also be purified.

The invention provides methods that utilize a solid phase based approach to capture polypeptides or other molecules of interest covalently via a cleavable linker such as a photo-cleavable linker that allows light catalyzed recovery of the captured molecules. The cleavable linker is constructed such that, upon cleavage, specific functional groups are transferred to the released molecules. Such functional groups include, for example, stable isotope tags that enable accurate peptide quantification by mass spectrometry based on isotope dilution theory, isotope distribution tags that identify the tagged peptides or fragments thereof by their isotope distribution, charged amino acids, or other compounds that mediate efficient ionization in a mass spectrometer and direct the fragmentation pattern in the collision cell of a tandem mass spectrometer. Furthermore, the method allows the chemical or enzymatic modification, de-modification, cleavage or other manipulation of the molecules such as polypeptides while they are immobilized on the solid support. Although a photo-cleavable linker is particularly useful, it is understood that any linker that can be specifically cleaved can be used, as disclosed herein. Alternatives to photo-cleavable linkers include acid and base cleavable linkers, linkers cleavable by heat and linkers containing a target cleavage site for enzymes, as described herein.

The methods of the invention are based on the advantageous use of solid phase chemistry to immobilize molecules from a sample and allow the convenient transfer of a label such as a tag to the captured sample molecules. The method is based on the attachment of a chemical group to a solid support. The chemical group has features, which are exemplified in FIG. 1. One feature of the chemical group is a cleavable functional group that allows reversible capture and release of a molecule. A second feature of the chemical group is one or more functional groups having desirable chemical properties. Such a functional group can be, for example, a label or tag convenient for subsequent analysis of the molecule or a chemical moiety that imparts a desirable chemical property on the molecule such as a change in charge, hydrophobicity, or mass. A third feature of the chemical group is a reactive group that allows covalent binding of the chemical group to a molecule in a sample. These three features are arranged on the chemical group such that a sample molecule can be captured via the reactive group and, upon cleavage, the functional groups are transferred to the released molecule (see FIG. 1).

The chemical group also contains a chemical moiety that allows the chemical group to be attached to a solid support while at the same time allowing the above-described features to be exploited. The chemical group having the above-described features can be synthesized on a solid support by sequential addition of chemical moieties imparting the features or can be synthesized as a chemical group and then attached to the solid support, if desired.

Figure 1B:
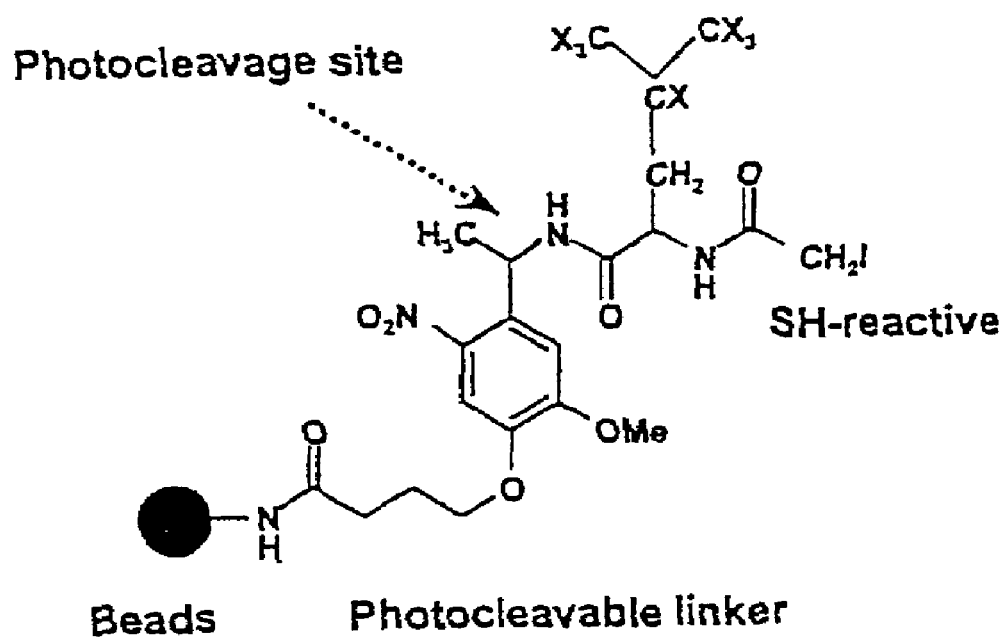
FIG. 1B shows a sulfhydryl-reactive solid-phase isotope tagging reagent. The o-nitrobenzyl-based photocleavable linker is coupled to aminopropyl glass beads. Peripheral to the photocleavable linker, an isotope tag represented as a leucine molecule containing either 7 hydrogen (H) or 7 deuterium (D), indicated by "X", is attached, followed by an iodoacetyl group as the SH-reactive group.
Figure 1C:
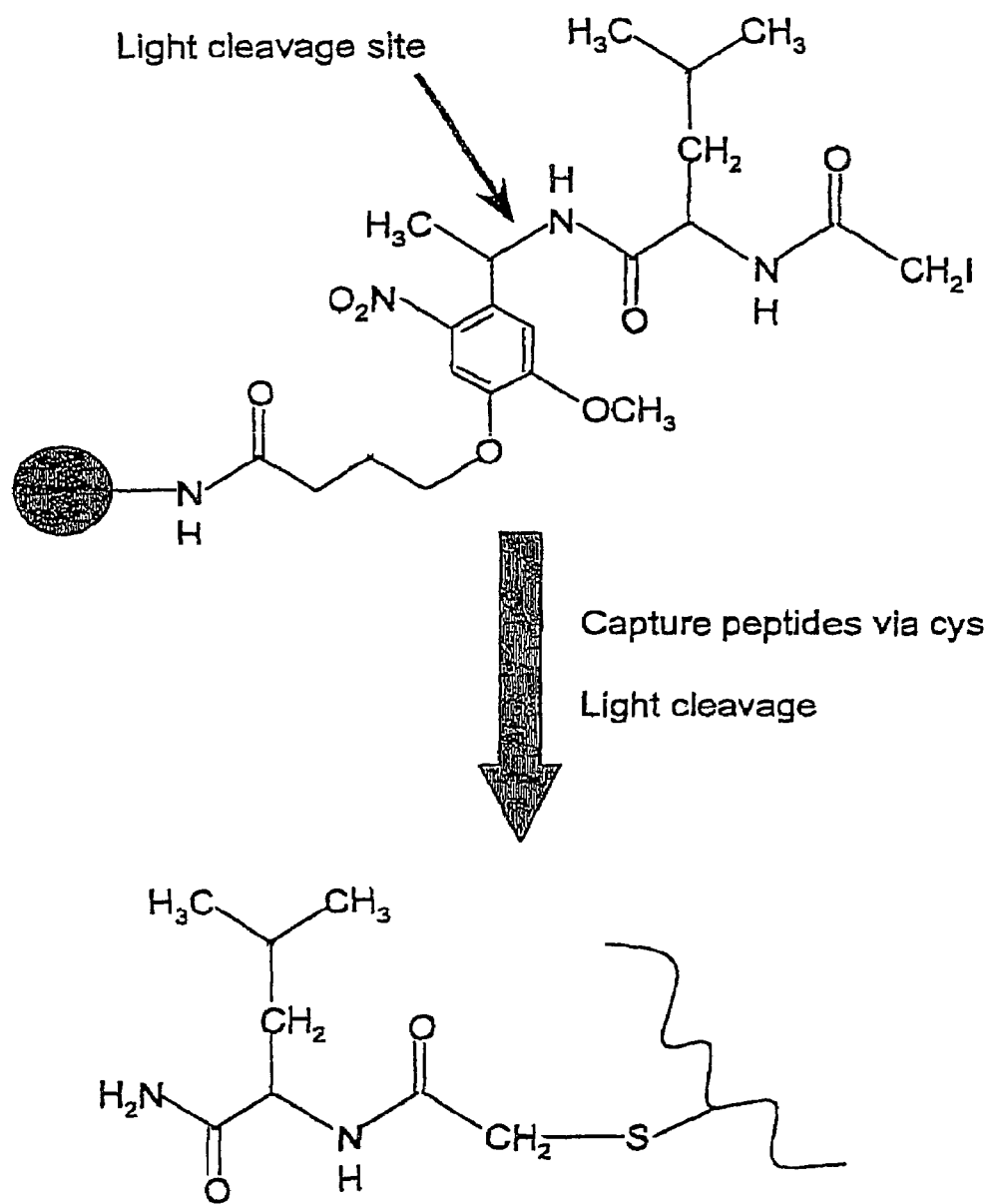
FIG. 1C shows the transfer of an isotope tag to a polypeptide following capture and release using the solid-phase isotope tagging method. The linker is constructed such that upon cleavage, specific functional groups are transferred to the released polypeptides.

A particular embodiment of a method of the invention is illustrated in FIG. 1. A chemical group having a cleavable functional group, one or more desired functional groups such as a tag, and a reactive group is coupled to the solid support. FIG. 1 shows a photo-cleavable linker with an amino functionality that is covalently attached to the solid support. This photo-cleavable linker allows light-initiated cleavage of molecules after they are captured on the solid phase. A linker molecule having desired specific functional groups is attached to the photo-cleavable linker via the amino functionality. Upon photo-cleavage, the linker molecule containing the functional groups is transferred to the captured molecule, represented as a peptide in FIG. 1C, resulting in the transfer of desirable functional groups to the molecule. For example, as disclosed herein, the functional group transferred can be a stable isotope coded amino acid useful for quantitative mass spectrometry. Extending from the functional linker having one or more functional groups is a reactive group with specificity for a chemical moiety on the molecule, for example, a group reactive with amino, sulfhydryl, carboxy, or other groups of a polypeptide.

A molecule, for example, a molecule in a sample, is contacted with the solid support having a chemical group attached as described above. The molecules are incubated under conditions that allow covalent binding of the sample molecule to the solid support via the chemical group. One skilled in the art can readily determine appropriate conditions for allowing covalent coupling based on the reactive group on the chemical group and on the sample molecule. Similarly, one skilled in the art can readily determine appropriate conditions for non-covalent interactions, as disclosed herein.

In the particular embodiment exemplified in Example I and shown in FIG. 1, the solid phase support is a controlled pore glass bead to which the photo-cleavable linker has been attached via a silane linkage. The photo-cleavable linker shown in FIG. 1 can be cleaved with 360 nm UV light. A deuterated or non-deuterated amino acid such as leucine can used as the functional groups to be transferred to the polypeptide exemplified in FIG. 1. If two different samples sources are used for a comparative or quantitative analysis, the two isotope tags will generally differ in mass by 7 or 10 mass units depending on the state of deuteration of leucine. As disclosed herein, other amino acids of different isotope distributions or molecules different from an amino acid can also be used as stable isotope tags. The peptide-reactive group shown in FIG. 1 is an iodoacetyl group that specifically reacts with sulfhydryl groups. Upon photo cleavage, the polypeptides illustrated in FIG. 1C are released with the addition of mass tags due to the modified leucine. Although exemplified with deuterated amino acids, it is understood that any suitable isotopic form, for example, isotopes of other constituent elements such as $^{13}C$, $^{15}N$, and the like, can be used in methods of the invention. Although non-radioactive isotopes are generally used, even radioactive isotopes such as tritium can be used.

The invention also provides reagents such as those exemplified in FIG. 1. The reagents can be used to isolate and tag sample molecules, including complex samples (see Example V). Thus, the invention provides a reagent containing a bead, a cleavable functional group, a functional group such as a tag, and a reactive group, as schematically shown in FIG. 1A.

Thus, the invention additionally provides a composition comprising a solid support coupled to a chemical group comprising a cleavable functional group, a functional group such as a tag and a reactive group covalently linked to a sample molecule, wherein the cleavable functional group, the tag and the reactive group are positioned relative to each other to allow transfer of the tag to the sample molecule upon cleavage of the cleavable functional group. The invention further provides a composition comprising a solid support covalently coupled to a chemical group comprising a cleavable functional group, a mass spectrometry tag and a reactive group for covalently attaching a sample molecule, wherein the cleavable functional group, the tag and the reactive group are positioned relative to each other to allow transfer of the tag to the sample molecule upon cleavage of the cleavable functional group.

The methods of the invention are advantageous in that they provide the ability to selectively isolate a molecule and transfer one or more functional groups, including a label or tag, onto the molecule upon release. Accordingly, the functionalities of the chemical group, that is, the cleavable functional group, one or more functional groups and the reactive group, are positioned relative to each other to allow transfer of a functional group such as a tag to the molecule. Therefore, the functionalities of the chemical group will generally be arranged so that the functional group, for example, a tag, is positioned between the cleavable functional group and the reactive group, as illustrated in FIG. 1, allowing transfer of the functional group to the captured molecule upon cleavage of the cleavable functional group and release of the molecule.

The methods of the invention are advantageous since they utilize the ability to capture sample molecules, transfer a functional group to the molecules, and release the molecules with an attached functional group. Thus, the methods can be used to label a sample molecule and concomitantly purify the sample molecule in a single step. The incorporation of a cleavable functional group facilitates the release of the sample molecule with the attached functional group, which can then be further analyzed. Although the methods of the invention generally use a cleavable functional group, it is understood that the methods of the invention can also be used to transfer a functional group such as a label or tag without the need to release the captured molecule prior to further analysis. Use of methods of the invention in the absence of a cleavable chemical group cleavable by a chemical or enzymatic reaction is applicable to analytical methods such as MS, in particular, MALDI-TOF, in which a laser is used to cleave an attached molecule and ionize the molecule at the same time.

The methods of the invention can readily be applied to a wide variety of molecules. As described above, in some cases, a molecule can have a reactive chemical moiety suitable for the capture methods disclosed herein. However, if desired, the molecules can be modified to incorporate a desirable functional group, in particular a reactive group suitable for the capture methods disclosed herein.

For example, polypeptides that do not contain cysteine residues, that is, do not contain the natural amino acids containing a sulfhydryl side chain, would not bind to the solid-phase reagents shown in FIG. 1. While it is desirable in some cases to selectively isolate cysteine-containing polypeptides, in other cases it is desirable to isolate, identify and quantify other or additional polypeptides contained in a sample. For example, it is possible to synthesize amino-reactive groups such as succinimide esters as the reactive group of the solid-phase reagent. Alternatively, the molecules to be captured can be chemically modified to incorporate a specific functional group.

For example, in a specific embodiment disclosed herein, the primary amine group of a polypeptide is modified to a sulfhydryl group, allowing the same SH-reactive solid phase beads as shown in FIG. 1 to be used to capture the polypeptide. In this strategy, an amino group of a polypeptide can be converted into a sulfhydryl group by the one-pot chemistry shown in FIG. 5. First, amino groups are modified by N-succinimidyl S-acetylthioacctate (SATA). Upon hydroxylamine treatment, followed by reduction with tris(2-carboxyethyl)phosphine (TCEP), the amino group of the peptide is converted into a sulfhydryl group. As exemplified herein, essentially every amino group in a sample molecule can be converted to a sulfhydryl group (see Example II). Modified peptides can be optionally purified, for example, by desalting on a C18 reverse phase cartridge, recovered and can then be attached to the beads such as those shown in FIG. 1.

Upon conversion of amino groups into sulfhydryl groups, the protonation site disappears. Therefore, charged amino acids such as lysine, instead of, for example, leucine, can be used to tag the polypeptides. In this way, the free amino group of the lysine side chain can provide the alternative site of protonation and the charge state of the peptide remains unchanged by this procedure. Other suitable groups for adding a tag containing a charged group include, for example, arginine, pyridyl, trimethylamine, and the like, which are strong bases in solution or gas phase, that is, groups that promote ionization. This is important since the charge state of peptides under typical mass spectrometry experiment affects the collision induced fragmentation in the mass spectrometer for peptide sequencing and detection.

Methods and chemistries for modifying amino acid side chains in polypeptides are well known to those skilled in the art (see, for example, Glazer et al., *Laboratory Techniques in Biochemistry and Molecular Biology: Chemical Modification of Proteins*, Chapter 3, pp. 68-120, Elsevier Biomedical Press, New York (1975), which is incorporated herein by reference; and Pierce Catalog (1994), Pierce, Rockford Ill.).

Methods for modifying the amino-terminus of a polypeptide can also be used. In addition to the method exemplified herein for modifying an amino group, including the N-terminus (see Example II), other methods for modifying the N-terminus are well known to those skilled in the art (see, for example, Brancia et al., *Electrophoresis* 22:552-559 (2001); Hoving et al., *Anal. Chem.* 72:1006-1014 (2000); Munchbach et al., *Anal. Chem.* 72:4047-4057 (2000), each of which is incorporated herein by reference).

In addition, a reactive group can be generated on a molecule, which can subsequently be modified to incorporate a desired chemical moiety. For example, cleavage by CNBr results in a homoserine lactone. Accordingly, a polypeptide containing methionine can be chemically cleaved by CNBr to generate a homoserine lactone. The resulting homoserine lactone can be modified by an amine, allowing incorporation of a chemical group having a reactive amine.

The molecules can be modified chemically or enzymatically, as desired. For example, the molecules can be chemically modified using methods such as those described above. In addition, the molecules can be modified enzymatically. A captured molecule can be enzymatically modified to incorporate or remove a group from the molecule. For example, a polypeptide can be phosphorylated by a kinase or dephosphorylated by a phosphatase, or by any other enzyme having the ability to posttranslationally modify a polypeptide resulting in the addition or removal of a chemical moiety from the molecule. Similarly, a nucleic acid can be modified after capture by any of the well known enzymes that add or remove chemical moieties to or from a nucleic acid (see, for example, Sambrook et al., *Molecular Cloning: A Laboratory Manual*, 2nd ed., Cold Spring Harbor Press, Plainview, N.Y. (1989); Ausubel et al., *Current Protocols in Molecular Biology* (Supplement 47), John Wiley & Sons, New York (1999); Sambrook and Russel, *Molecular Cloning: A Laboratory Manual*, 3rd ed., Cold Spring Harbor Press, Cold Spring Harbor (2001)). Exemplary enzymes useful for modifying a captured molecule, including polypeptides or nucleic acids, include kinases, phosphatases, methylases, decarboxylases, and the like, or any enzyme capable of adding or removing a chemical moiety to or from a captured molecule.

Any of a variety of reactive groups can be incorporated into a chemical group for reacting with a sample molecule so long as the reactive group can be covalently coupled to a molecule such as a polypeptide. Reactive groups are well known to those skilled in the art (see, for example, Hermanson, supra, 1996; Glazer et al., *Laboratory Techniques in Biochemistry and Molecular Biology: Chemical Modification of Proteins*, Chapter 3, pp. 68-120, Elsevier Biomedical Press, New York (1975); Pierce Catalog (1994), Pierce, Rockford Ill.). For example, a reactive group can react with carboxyl groups found in Asp or Glu, or the reactive group can react with other amino acids such as His, Tyr, Arg, and Met. A reactive group can also react with amines such as Lys, for example, imidoesters and N-hydroxysuccinimidyl esters. In addition, a reactive group can also react with oxygen or sulfur using chemistry well known in the art. A reactive group can also react with a phosphate group for selective labeling of phosphopeptides, or with other covalently modified peptides, including glycopeptides, lipopeptides, or any of the covalent polypeptide modifications disclosed herein. Additionally, one skilled in the art will know or can readily determine conditions for modifying polypeptides using known reagents, incubation conditions and time of incubation to obtain conditions optimal for modification of polypeptides or other molecules for use in methods of the invention.

An exemplary sulfhydryl reactive group includes an iodoacetamido group (see Gygi et al., *Nature Biotechnol.* 17:994-999 (1999)). Other examplary sulfhydryl reactive groups include maleimides, alkyl and aryl halides, haloacetyls, α-haloacyls, pyridyl disulfides, aziridines, acrylolyls, and arylating agents. If desired, the polypeptides can be reduced prior to reacting with a reagent of the invention, which is particularly useful when the reagent contains a sulfhydryl reactive group.

A reactive group can also react with amines such as the α-amino group of a peptide or the ε-amino group of the side chain of Lys, for example, imidoesters, N-hydroxysuccinimidyl esters (NHS), isothiocyanates, isocyanates, acyl azides, sulfonyl chlorides, aldehydes, ketones, glyoxals, epoxides, oxiranes, carbonates, arylating agents, carbodiimides, anhydrides, and the like. A reactive group can also react with carboxyl groups found in Asp or Glu or the C-terminus of a peptide, for example, diazoalkanes, diazoacetyls, carbonyldiimidazole, carbodiimides, and the like. A reactive group that reacts with a hydroxyl group includes, for example, epoxides, oxiranes, carbonyldiimidazoles, N,N'- disuccinimidyl carbonates, N-hydroxycuccinimidyl, chloroformates, and the like. A reactive group can also react with amino acids such as His, Tyr, Arg, and Met. In addition, a reactive group can also react with a phosphate group for selective labeling of phosphopeptides, or with other covalently modified peptides, including glycopeptides, lipopeptides, or any of the known covalent polypeptide modifications. One skilled in the art can readily determine conditions for modifying sample molecules by using various reagents, incubation conditions and time of incubation to obtain conditions optimal for modification of sample molecule for use in methods of the invention.

The methods of the invention are advantageous in that, by capturing sample molecules, various chemical and/or enzymatic modifications can be performed on the attached molecules while the sample molecules remain bound to the solid support. Because the sample molecules remain bound to the solid support during physical, chemical and/or enzymatic manipulations, the yield of modified sample molecules is higher than solution phase methods. Thus, the methods of the invention can be used to capture at least about 5%, about 10%, about 20%, about 30%, about 40%, about 50%, about 60%, about 70%, about 80%, about 90%, about 95%, about 98%, about 99%, or even essentially all of a particular class or classes of molecules having a chemical property capable of reacting with the reacting group of the solid phase capture and tag reagents of the invention. Furthermore, the methods of the invention can be used to capture and release at least about 5%, about 10%, about 20%, about 30%, about 40%, about 50%, about 60%, about 70%, about 80%, about 90%, about 95%, about 98%, about 99% or even essentially all of a particular class or classes of molecules in a sample that are contacted with and bound to the solid support of the invention containing a capture and tag reagent. For example, as disclosed herein, essentially 100% of the molecule can be captured and released (see Example I). One skilled in the art can readily determine conditions optimized for capturing sample molecules and/or releasing sample molecules from the solid support.

The invention further provides a method for labeling a molecule. The method includes the steps of contacting a sample molecule with a solid support coupled to a chemical group comprising a cleavable functional group, one or more functional groups, and a reactive group for the sample molecule, under conditions allowing the sample molecule to covalently bind to the reactive group; modifying the sample molecule bound to the solid support; and cleaving the cleavable functional group, thereby releasing the modified sample molecule comprising one or more functional groups.

The methods of the invention can be used to modify captured molecules, as desired. For example, the methods can be used to capture polypeptides from a sample including both phosphorylated and non-phosphorylated polypeptides. A method systematically analyzing protein phosphorylation has recently been described (Zhou et al., *Nature Biotechnol.* 19:375-378 (2001)). Rather than carrying out chemical reactions in solution as in Zhou et al., the polypeptides can first be captured using the methods disclosed herein and modified while attached to the solid support (see Example IV). Alternatively, the methods disclosed herein for capturing and labeling a molecule can be applied after performing the reactions described in Zhou et al., supra, 2001, or any other chemical or enzymatic modifications.

The compositions and methods of the invention can be advantageously used in a variety of applications. One particularly useful application is quantitative protein expression analysis. For example, the methods and reagents disclosed herein can be used to impart specific isotopic signatures to a molecule such as a polypeptide contained in a complex sample. In one particular application of quantitative analysis, two or more samples can be compared (see FIG. 8, Example III). Quantitative analysis of peptides from two different samples can be achieved based on the concept of stable isotope dilution in a similar fashion as the ICAT technology for relative quantification of protein expression (Gygi et al., *Nature Biotechnol.* 17:994-999 (1999); see Example V). A differentially isotopically labeled molecule can be used to label two samples for comparison, for example, an amino acid such as a deuterated leucine or non-deuterated leucine, or other amino acids, which can be incorporated as mass tags for two different samples. The methods of the invention are advantageous in that both isolation of a molecule and incorporation of a tag such as a stable isotope are both achieved. Thus, the methods of the invention are particularly useful for quantitative mass spectrometric analysis.

As disclosed herein, incorporation of functional groups to a polypeptide can also be achieved through the amino groups of a peptide, which is particularly useful if the polypeptide to be analyzed does not contain free cysteine residues when applying a capture method based on the presence of sulfhydryl groups in a polypeptide. Since most polypeptides contain at least one amino group at its N-terminus, even polypeptides with no cysteine residues can be labeled with the solid phase based method to incorporate sulfhydryl groups into the polypeptide. In the case of a polypeptide in a sample having a blocked amino-terminus, such polypeptides can be fragmented to generate a free amino terminus on the cleaved fragments. Thus, the methods of the invention can be applied to the isolation of a variety of molecules using specific chemical modifications.

Furthermore, there is great structural flexibility in the choice of the transferred tags. The structure of the tag can therefore be deliberately chosen to achieve specific objectives. For example, very polar peptides can be made more hydrophobic and therefore better retained on reverse-phase columns by the transfer of a hydrophobic tag, a strong gas-phase basic group such as pyridyl can be transferred to direct fragmentation in the collision cell of a mass spectrometer, or elements with characteristic isotope distribution such as chlorine or bromine can be added to provide distinct isotopic signatures for the tagged peptides.

The methods of the invention can also be applied to the analysis of modified molecules, for example, polypeptides modified by post-translational modifications. For example, the methods can be applied to quantitative analysis of protein phosphorylation. Methods for the systematic analysis of protein phosphorylation has been previously described (Zhou et al., *Nature Biotechnol.* 19:375-378 (2001)). A sequence of chemical reactions is carried out in solution for the selective isolation of phosphorylated peptides from complex peptide solutions containing phosphorylated and non-phosphorylated polypeptides in solution (Zhou et al., supra, 2001). The methods disclosed herein using solid phase capture and release can also be used for the selective isolation of phosphopeptides. Phosphorylated and non-phosphorylated polypeptides are captured on the solid phase beads, as disclosed herein. Once immobilized, a sequence of chemical reactions is carried out that lead to phosphate-specific labeling of phosphopeptides (Zhou et al., supra, 2001). The peptides are released by cleavage, imparting a stable isotope signature to each peptide for accurate quantification. The originally phosphorylated polypeptides, now converted to sulfhydryl groups, can be captured using the methods disclosed herein for isolating a sulfhydryl-containing molecule. The captured polypeptides can be washed free of non-phosphorylated peptides and released, for example, for mass spectrometric analysis. The methods of the invention disclosed herein have obvious advantages over the solution chemistry as the number of sample handling steps required to remove excess reagents after each chemical reaction are dramatically reduced and simplified.

In addition to phosphorylation, the methods of the invention can be readily applied to polypeptides having many different forms of post-translational modifications such as glycosylation, ubiquitination, acetylation, palmitylation, myristylation, and the like, as disclosed herein. The methods of the invention can thus be used to selectively isolate other post-translationally modified molecules, including polypeptides, with concomitant transfer of various functional groups to the peptides. Selective isolation of a particular type of post-translational modification can be achieved using methods of the invention. For example, an antibody having specific binding activity for ubiquitination can be used to isolate ubiquitinated polypeptides, allowing quantitative analysis of ubiquitination of polypeptides in much the same fashion of quantitative analysis of protein phosphorylation is achieved. Such methods can also be applied to other modifications of molecules, if desired.

Antibodies can also be used for subsequent analysis and/or isolation of sample molecules modified with an epitope tag. Methods for preparing antibodies are well known to those skilled in the art. The term antibody is used in its broadest sense to include polyclonal and monoclonal antibodies, as well as antigen binding fragments of such antibodies. An antibody useful in the invention, or antigen binding fragment of such an antibody, is characterized by having specific binding activity for a polypeptide or a peptide portion thereof of at least about $1\times10^5$ $M^{-1}$. Thus, Fab, F(ab')$_2$, Fd, Fv, single chain Fv (scFv) fragments of an antibody and the like, which retain specific binding activity for a polypeptide. Specific binding activity of an antibody for a polypeptide can be readily determined by one skilled in the art, for example, by comparing the binding activity of an antibody to a particular antigen versus a control antigen. Methods of preparing polyclonal or monoclonal antibodies and determining binding activity and/or specificity are well known to those skilled in the art (see, for example, Harlow and Lane, *Antibodies: A Laboratory Manual*, Cold Spring Harbor Laboratory Press (1988)).

Although the methods of the invention have generally been exemplified herein with polypeptides, it is understood that any of a variety of molecules in a sample can be readily labeled by the methods disclosed herein. In general, many classes of biomolecules such as oligonucleotides, metabolites, and the like, can be functionalized by the methods disclosed herein to incorporate desirable functional groups for improved qualitative or quantitative analysis. Therefore, the methods disclosed herein, allowing reversible capture and transfer of specific functional groups to a molecule is generally useful in many applications in the field of proteomics, other types of discovery science and quantitative biological analyses in general.

The methods of the invention can be used to efficiently capture and release a class of molecules such as polypeptides, nucleic acids, lipids, second messengers, metabolites, and the like, or a subset of such a class of molecules. If desired, the methods of the invention can also be used to capture two or more classes of molecules and/or a subset of those classes of molecule. For example, the methods can be used to capture both polypeptides and nucleic acids, or any combination of two or more classes of molecules, as desired.

The invention also provides a method for analyzing a molecule. The method includes the steps of contacting a sample molecule with a solid support coupled to a chemical group comprising a cleavable functional group, one or more functional groups, and a reactive group for the sample molecule, under conditions allowing the sample molecule to covalently bind to the reactive group; cleaving the sample molecule from the solid support, wherein one or more specific functional groups are transferred to the released sample molecule; and analyzing the released sample molecule. Any of a variety of analytical methods can be used including, for example, mass spectrometry, sequencing, liquid chromatography, spectrophotometry, fluorentry, and the like. The methods of the invention are advantageous since the molecules can be covalently captured, allowing extensive washing to remove non-analyte materials prior to analysis. Furthermore, the functional groups to be transferred to the captured molecules can incorporate a functionality useful for facilitating further analysis of the molecules, for example, by adding a chromophore, fluorphore, mass tag, and the like.

Mass spectrometry is a particularly useful method for analyzing sample molecules. A variety of mass spectrometry systems can be employed to analyze sample molecules captured using the methods of the invention. Mass analyzers with high mass accuracy, high sensitivity and high resolution can be used and include, but are not limited to, matrix-assisted laser desorption time-of-flight (MALDI-TOF) mass spectrometers, electrospray ionization time-of-flight (ESI-TOF) mass spectrometers and Fourier transform ion cyclotron mass analyzers (FT-ICR-MS). Other modes of MS include ion trap and triple quadrupole mass spectrometers. In ion trap MS, analytes are ionized by electrospray ionization or MALDI and then put into an ion trap. Trapped ions can then be separately analyzed by MS upon selective release from the ion trap. Fragments can also be generated in the ion trap and analyzed. The sample molecules labeled with a mass tag using methods of the invention can be analyzed, for example, by single stage mass spectrometry with a MALDI-TOF or ESI-TOF system. Furthermore, LC-MS/MS or LC-ESI-TOF can be used. It is understood that any MS methods and any combination of MS methods can be used to analyze a sample molecule. Methods of mass spectrometry analysis are well known to those skilled in the art (see, for example, Yates, *J. Mass Spect.* 33:1-19 (1998); Kinter and Sherman, *Protein Sequencing and Identification Using Tandem Mass Spectrometry*, John Wiley & Sons, New York (2000)).

The methods of the invention can be used to analyze molecules in a sample. The sample can be derived, for example, from a biological specimen. A specimen refers specifically to a sample obtained from an organism or individual. A specimen can be obtained from an individual as a fluid or tissue specimen. For example, a tissue specimen can be obtained as a biopsy such as a skin biopsy, tissue biopsy or tumor biopsy. A fluid specimen can be blood, serum, urine, saliva, cerebrospinal fluid or other bodily fluids. A fluid specimen is particularly useful in methods of the invention since fluid specimens are readily obtained from an individual. Methods for collection of specimens are well known to those skilled in the art (see, for example, Young and Bermes, in *Tietz Textbook of Clinical Chemistry*, 3rd ed., Burtis and Ashwood, eds., W.B. Saunders, Philadelphia, Chapter 2, pp. 42-72 (1999)). A specimen can also be a microbiological specimen, which can be derived from a culture of the microorganisms, including those cultured from a specimen from an individual. Thus, the methods of the invention can be used to analyze complex mixtures in biological samples.

Although the methods of the invention are advantageous in that complex biological samples can be analyzed directly, a sample can also be processed, if desired. For example, a blood sample can be fractionated to isolate particular cell types, for example, red blood cells, white blood cells, and the like. A serum sample can be fractionated to isolate particular types of proteins, for example, based on structural or functional properties such as serum proteins modified by glycosylation, phosphorylation, or other post-translational modifications, or proteins having a particular affinity, such as an affinity for nucleic acids. A serum sample can also be fractionated based on physical-chemical properties, for example, size, pI, and the like. A serum sample can additionally be fractionated to remove bulk proteins present in large quantities, such as albumin, to facilitate analysis of less abundant serum polypepties. Furthermore, a cellular sample can be fractionated to isolate subcellular organelles. Moreover, a cellular or tissue sample can be solubilized and fractionated by any of the well known fractionation methods, including chromatographic techniques such as ion exchange, hydrophobic and reverse phase, size exclusion, affinity, hydrophobic charge-induction chromatography, and the like (Ausubel et al., supra, 1999; Scopes, *Protein Purification: Principles and Practice*, third edition, Springer-Verlag, New York (1993); Burton and Harding, *J. Chromatoar. A* 814:71-81 (1998)).

Although the methods of the invention are particularly useful for analyzing complex samples such as biological samples (see Example V), the methods can also be used on samples of reduced complexity. For example, the sample can be fractionated, as described above, to provide a smaller number of sample molecules to be captured on solid phase, including prior affinity chromatography. In addition, the sample can be a highly purified sample, including essentially a single purified molecule such as a polypeptide or nucleic acid or molecule that is expressed at high levels in the sample, for example, by recombinant methods.

The methods of the invention can be readily adapted to automation. For example, automated sampling, robotics, or any suitable automation methods can be applied to methods of the invention, if desired. Since all the reactions can be done easily in an automated fashion, the methods permit a high throughput sample preparation. In addition, since there is virtually no sample handling such as transferring steps, loss of captured molecules is minimized, thus improving the yield of molecule recovery. The captured molecules can also be extensively washed to remove non-captured sample molecules or any regents since the captured sample molecules remain bound to the solid support during the wash steps. The methods of the invention can be used to capture essentially all of a class or multiple classes of molecules from a sample, or a portion of the molecules from a sample, as desired.

The methods of the invention can be used to determine the expression level of molecules in a sample. The expression level refers to the amount of a molecule in a sample. The expression level of a molecule can be representative of the amount of messenger RNA (mRNA) encoded by a gene, the amount of polypeptide corresponding to a given amino acid sequence encoded by a gene, or the amount of a biochemical form of a molecule accumulated in a cell, including, for example, the amount of particular post-synthetic modifications of a molecule such as a polypeptide, nucleic acid or small molecule. The expression level can refer to an absolute amount of a molecule in a sample or to a relative amount of the molecule compared to a standard, including amounts determined under steady-state or non-steady-state conditions. The expression level of a molecule can be determined relative to a control component molecule in a sample. The expression level can be determined by direct comparison of two or more samples, as disclosed herein (see Example III).

As disclosed herein, the solid phase can be a glass bead such as a controlled pore glass bead (see Example I). However, any suitable solid support useful for binding sample molecules and carrying out the desired chemistry and washing conditions can be used. The solid support can thus be glass, derivatized glass, silicon, plastic or other substrates. Any solid phase materials suitable for solid phase chemical synthesis are useful as solid supports in methods of the invention. The solid supports can be porous or non-porous materials, surface films, magnetic beads, colloids, membranes and the like. The solid supports can be in the form of beads, flat surfaces, or any configuration suitable for capturing molecules using the methods disclosed herein. The solid support can be derivatized to incorporate chemical moieties suitable for coupling to other chemical groups, as desired.

The invention also provides kits containing reagents or compositions of the invention. Thus, the invention provides a kit with a solid-phase capture and tag reagent, exemplified as in FIG. 1. The contents of the kit of the invention, for example, a solid-phase capture and tag reagent or composition of the invention, are contained in packaging material, and, if desired, a sterile, contaminant-free environment. In addition, the packaging material contains instructions indicating how the materials within the kit can be employed to label sample molecules. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

It is understood that modifications which do not substantially affect the activity of the various embodiments of this invention are also included within the definition of the invention provided herein. Accordingly, the following examples are intended to illustrate but not limit the present invention.

EXAMPLE I

Attachment of Cysteine-Containing Peptide to a Solid Support and Recovery

This example describes the attachment of a cysteine-containing peptide to beads and recovery of a modified peptide by photo-cleavage.

A schematic diagram illustrating the attachment of a cysteine-containing peptide to the solid phase beads and recovery of the modified peptide via photo-cleavage is shown in FIG. 1C. A method was devised for site-specific, stable isotopic labeling of cysteinyl peptides using a solid-phase isotope tagging reagent (FIG. 1). The o-nitrobenzyl-based photocleavable linker was first attached to aminopropyl-coated glass beads by solid-phase peptide synthesis (Holmes and Jones, *J. Org. Chem.* 60:2318-2319 (1995)). Next, the isotope tag, a leucine molecule containing either seven hydrogen (d0) or seven deuterium atoms (d7), was attached to the photocleavable linker, again by solid-phase peptide synthesis (Holmes and Jones, supra, 1995). Finally, a sulfhydryl-specific iodoacetyl group was attached.

To demonstrate the capture and modification of a cysteine-containing peptide, commercially available laminin B peptide with the sequence CDPGYIGSR (SEQ ID NO:1; molecular weight 967) was used. Briefly, a sample consisting of 1 nmol of cysteine-containing laminin B peptide (CDPGYIGSR; SEQ ID NO:1) and 500 pmol non-cysteine-containing phosphoangiotensin (DRVY*IHPF, SEQ ID NO:2, with asterisk indicating phosphorylated tyrosine) was used. Peptides were reduced with 5 mM tris(carboxyethyl) phosphine (TCEP) in 100 μl of 0.2 M Tris (pH 8.0), 10 mM ethylenediamine tetraacetic acid (EDTA) for 30 min at room temperature.

Figure 2A:
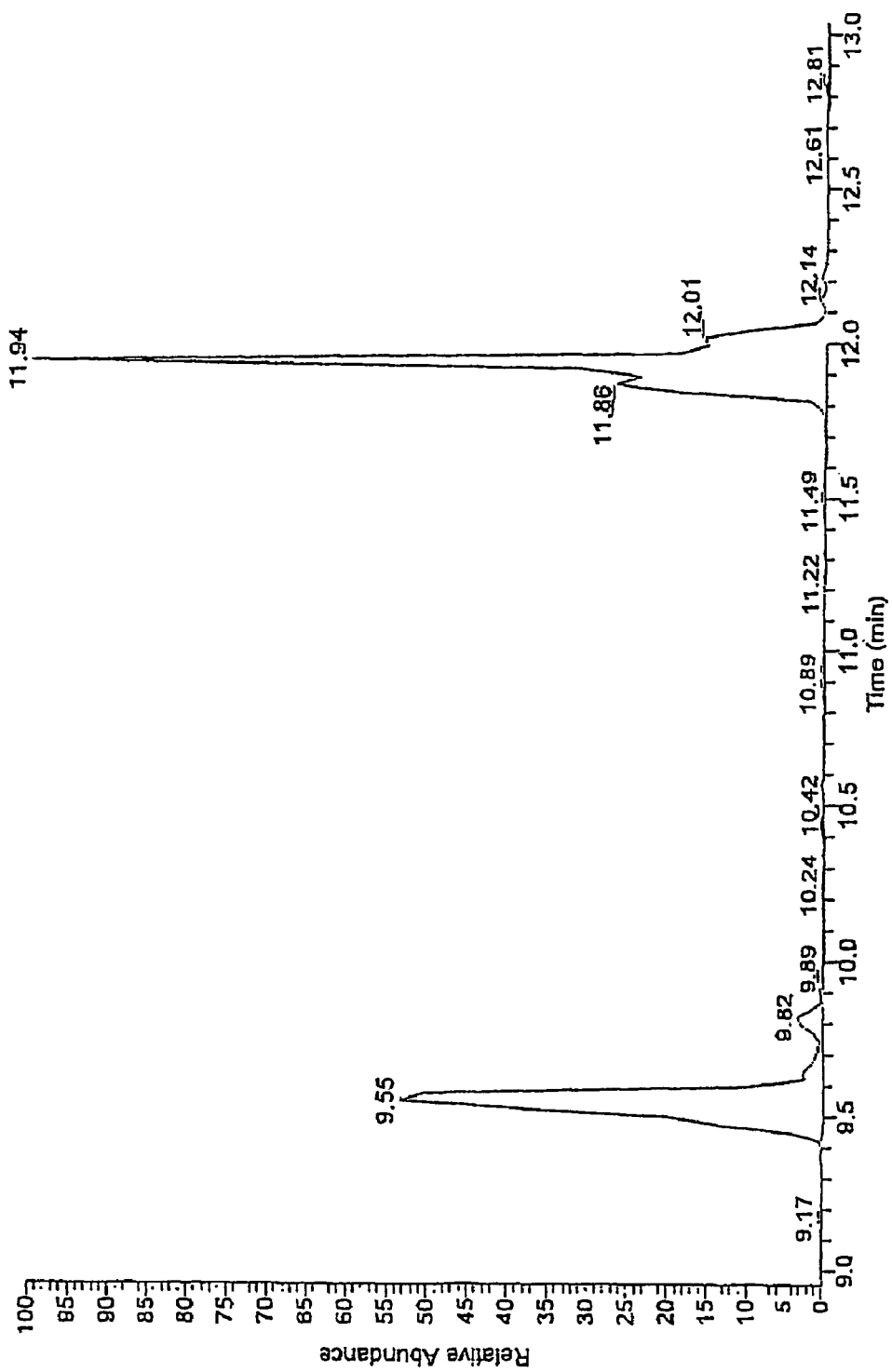
FIG. 2A shows LC analysis by reverse phase HPLC of a mixture of laminin B and control phosphoangiotensin,(RT: 8.95-13.04, NL: 1.22E7 Base Peak MS tcep30min).
Figure 2B:
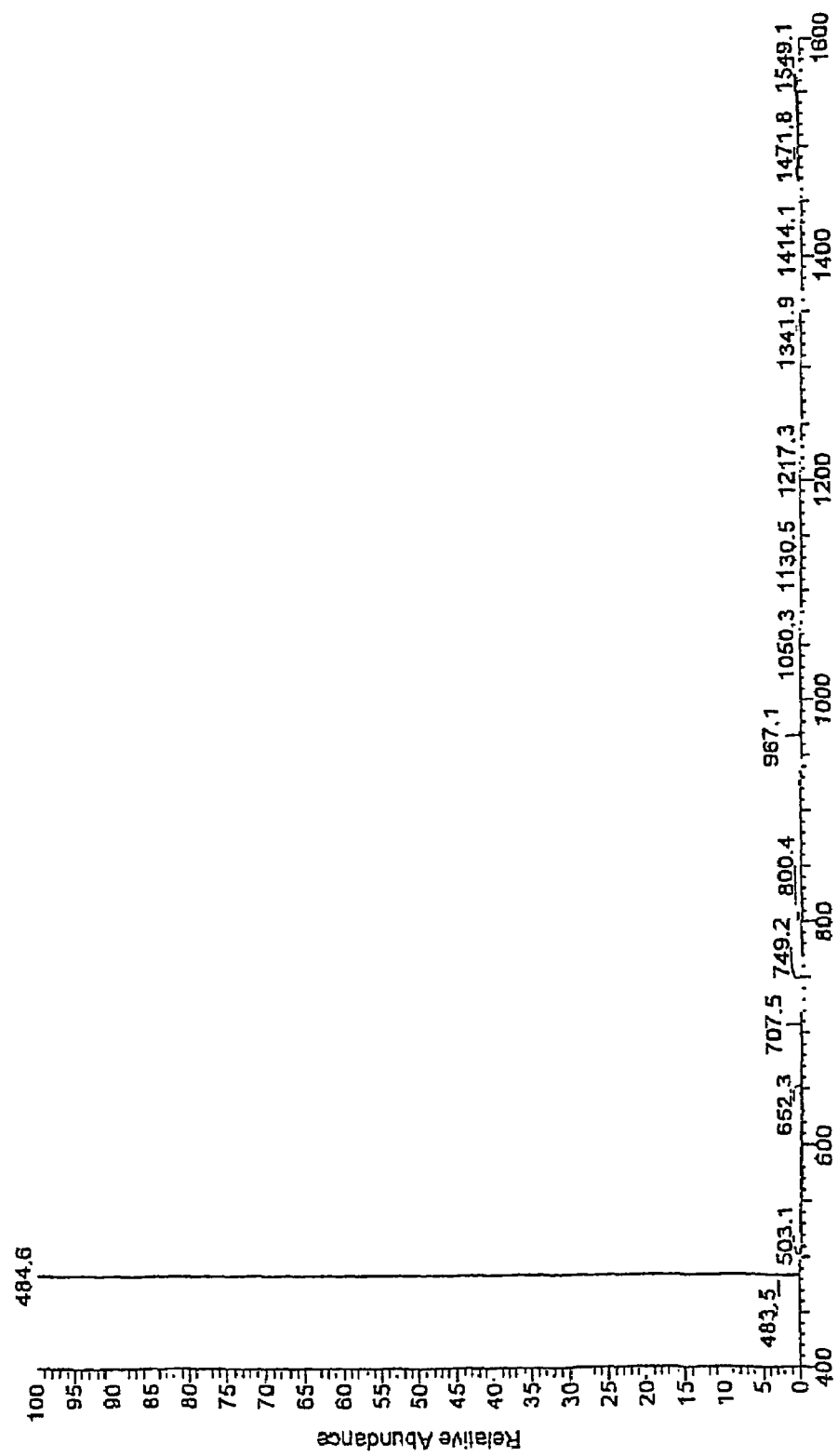
FIG. 2B shows electrospray ionization MS analysis of TCEP treated laminin B, (tcep30min #384, RT: 9.55, AV: 1, NL: 6.50EB, T: +c ESI Q3MS [400.00-1600.00]).

The peptide was analyzed by liquid chromatography. on reverse phase HPLC and mass spectrometry (LC-MS). The peptide was reduced by tris(2-carboxyethyl)phosphine (TCEP) and detected as a single peak eluting at 9.55 min with a mass to charge ratio (m/z) of m/z=484.6 for a doubly charged ion, as expected (see FIG. 2). A second peak eluting at 11.94 min is another standard peptide, namely phosphoangiotensin, with the sequence DRVYIHPF (SEQ ID NO:2; molecular weight 1126) that was added to the sample as a control. Phosphoangiotensin does not contain cysteine and was observed with the expected mass.

A solid phase support bead of controlled pore glass was modified by covalently attaching a photo-cleavable linker with an amino functionality (see FIG. 1). The photocleavable linker was attached to the solid support via a silane linkage. The reactive group is an iodoacetyl group that specifically reacts with sulfhydryl groups. Glass beads functionalized with amino groups (Sigma Aldrich; St Louis Mo.) were used as the solid support. Fmoc protected photolinker (4-[4-(1-(Fmocamino)ethyl)-2-methoxy-5-nitrophenoxy) butanoic acid or Fmoc-aminoethyl-photolinker; NovaBiochem, affiliate of Merck KGaA; Darmstadt Germany) and leucine were attached sequentially to the amino group functionalized beads via carbodiimide chemistry under standard solid phase peptide synthesis procedures. Fmoc protection on the leucine was then removed by piperidine treatment, and the free α-amino group of leucine was reacted with iodoacetic anhydride to create the reactive iodoacetyl group.

Briefly, the solid-phase isotope labeling beads were synthesized as follows. Unless otherwise noted, chemicals were purchased from Aldrich (Milwaukee, Wis.). First, 0.5 g of aminopropyl-coated controlled-pore glass beads (amine content ~400 μmol/g; Sigma, St. Louis, Mo.) were washed with anhydrous dimethylformamide (DMF). Then 600 μmol each of 1-hydroxybenzotriazole (HOBt; Nova Biochem, Laufelfingen, Switzerland), Fmoc-aminoethyl photolinker (Nova Biochem), and diisopropylcarbodiimide (DIC) were mixed for 30 min at room temperature, and this mixture was added to the beads for 90 min. The beads were then washed sequentially with DMF and dichloromethane and capped with 2 ml 40% acetic anhydride/60% pyridine in dichloromethane for 30 min. The beads were washed again with DMF and treated with 20% piperidine in DMF for 30 min to remove Fmoc protection. This process was repeated to attach Fmoc-leucine (Nova Biochem) as the isotope tag. Finally, the iodoacetyl group was attached to the beads as described previously (Zhou et al., Nat. Biotechnol. 19:375-378 (2001)). Beads were washed successively with DMF, water, and methanol, dried under reduced pressure, and stored at room temperature in the dark. For synthesis of beads with heavy isotope, Fmoc-d7-leucine was prepared from d7-leucine (Isotec, Miamisberg, Ohio) and Fmoc-N-hydroxysuccinimide (Nova Biochem) essentially as described previously (Lapatsanis et al., Synthesis 671-673 (1983)) except that the recrystallization step to purify Fmoc-leucine was omitted.

Five milligrams of the beads prepared as described above (2 μmol binding capacity) were used to capture peptides in a volume of 100 μl under constant agitation. Aliquots (1 μl) of the supernatant were removed from the reaction mixture for μLC-MS analysis before addition of the beads and at different time points after their addition. After 15 min of incubation, the beads were inactivated by the addition of 2 μl of β-mercaptoethanol for 5 min and washed sequentially with 2.0 M sodium chloride, methanol, and water. For photocleavage, the beads were resuspended in 100 μl of 0.2 M Tris (pH 8.0), 10 mM EDTA, 2% β-mercaptoethanol. Phosphoangiotensin (500 pmol) was added as an internal standard. Light from the Blak-Ray long-wave UV lamp (100 W, VWR Scientific, West Chester, Pa.) was filtered by 10% copper (II) sulfate solution (1 cm path length) and used to illuminate the beads from a distance of 10 cm. At different time points of illumination, an aliquot of 1 μl was taken from the supernatant for μLC-MS analysis. Beads were occasionally agitated to ensure uniform light illumination. The use of β-mercaptoethanol in the photocleavage buffer prevents possible methionine oxidation during photocleavage.

Figure 3A:
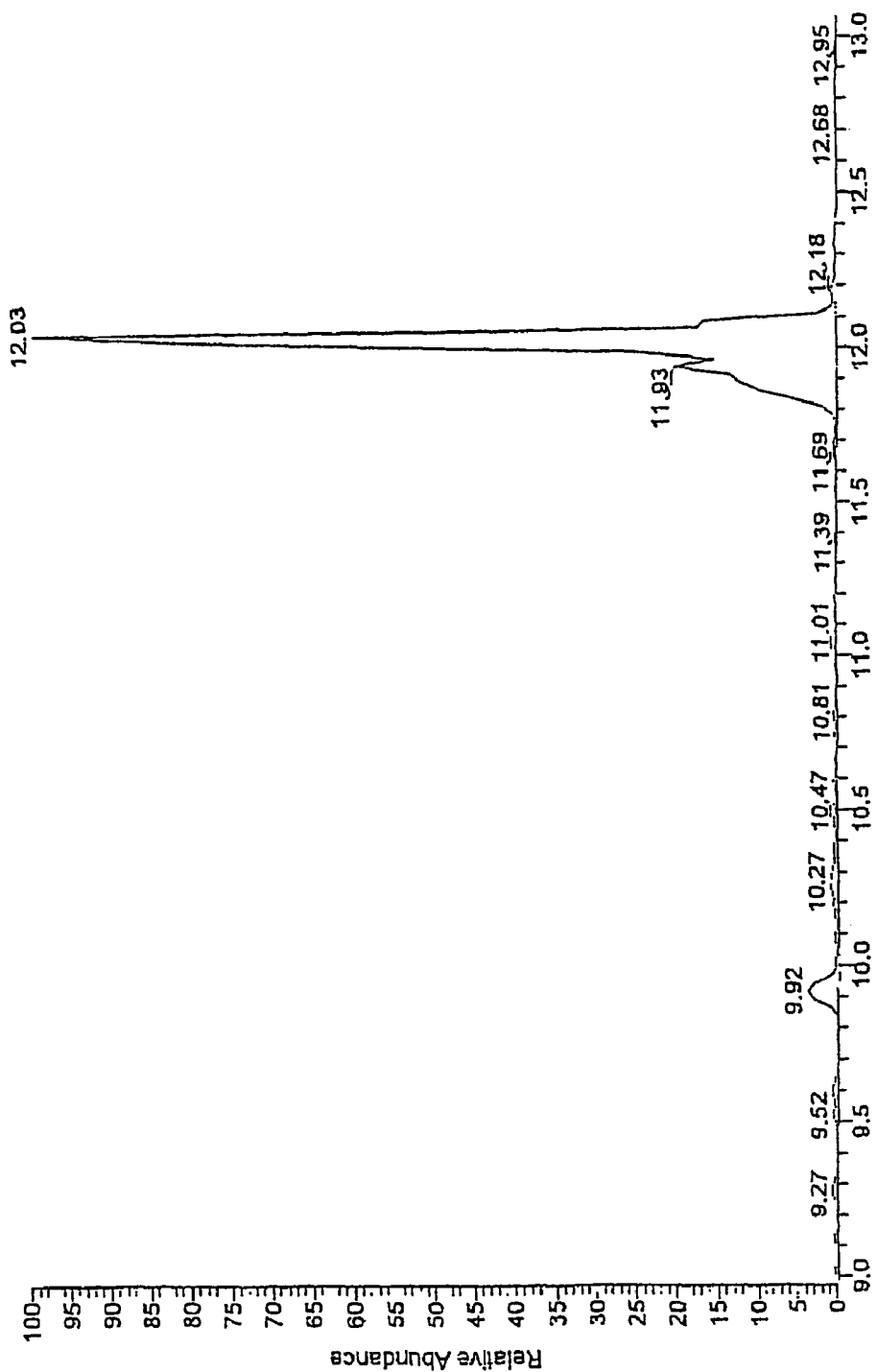
FIG. 3A shows LC analysis of an aliquot of the supernatant as treated in FIG. 2, (RT: 8.97-13.08, NL: 1.84E7 Base Peak MS 60minbeads).
Figure 3B:
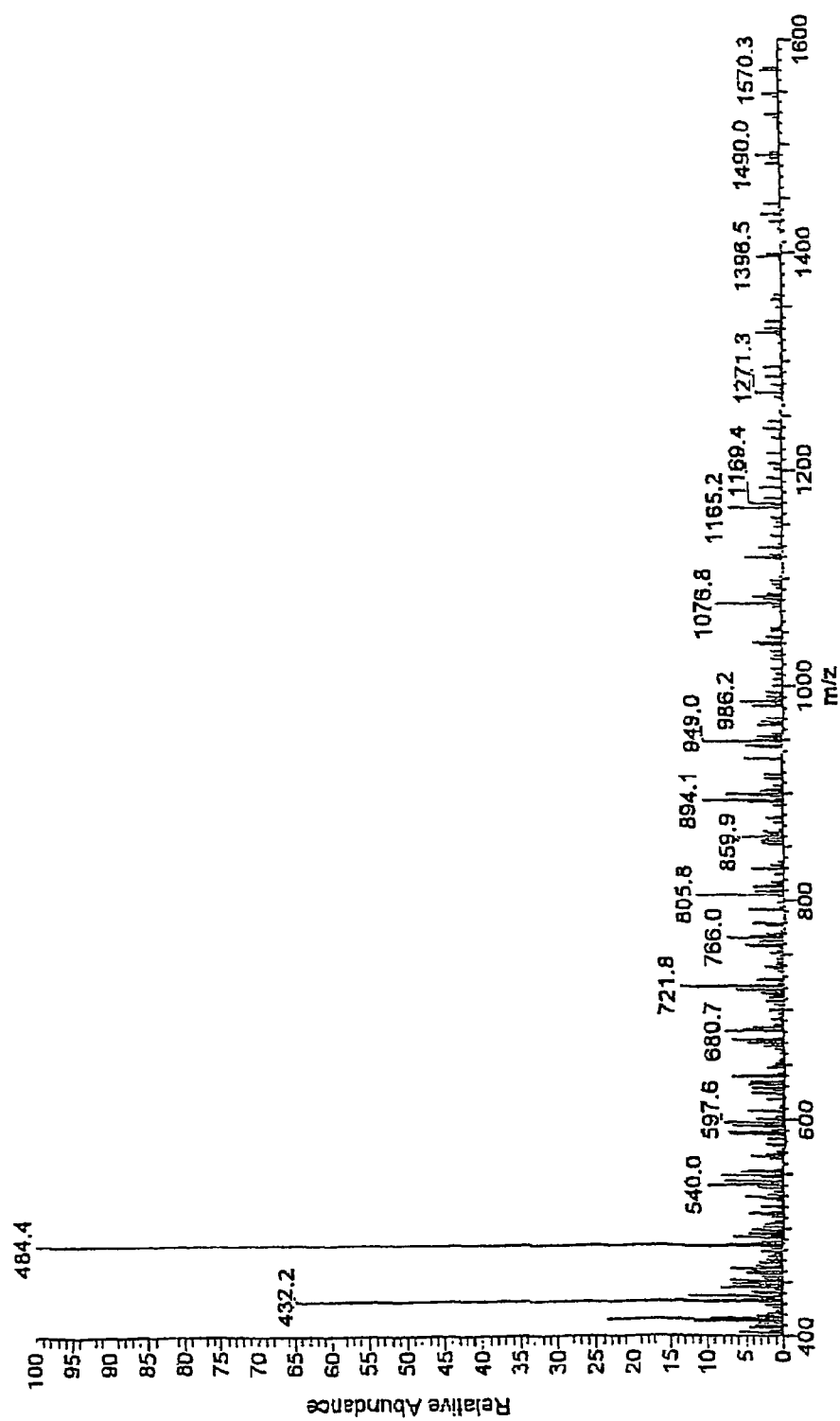
FIG. 3B shows MS analysis of the 9.62 min LC fraction of FIG. 3A having a retention time consistent with reduced laminin B, (60minbeads #387 RT: 9.62, AV:1, NL: 1.14E5, T: +c ESI Q3MS [400.00-1600.00]). The amount of laminin B was reduced due to binding to beads.

After incubating the peptides with the beads, as shown in FIG. 1, an aliquot of the supernatant was again analyzed by LC-MS. Data are shown in FIG. 3. As expected, only the non-cysteine containing phosphoangiotensin peptide was present in the supernatant, while the cysteine-containing laminin B peptide had disappeared completely from the solution, presumably due to quantitative capture by the beads.

Figure 4A:
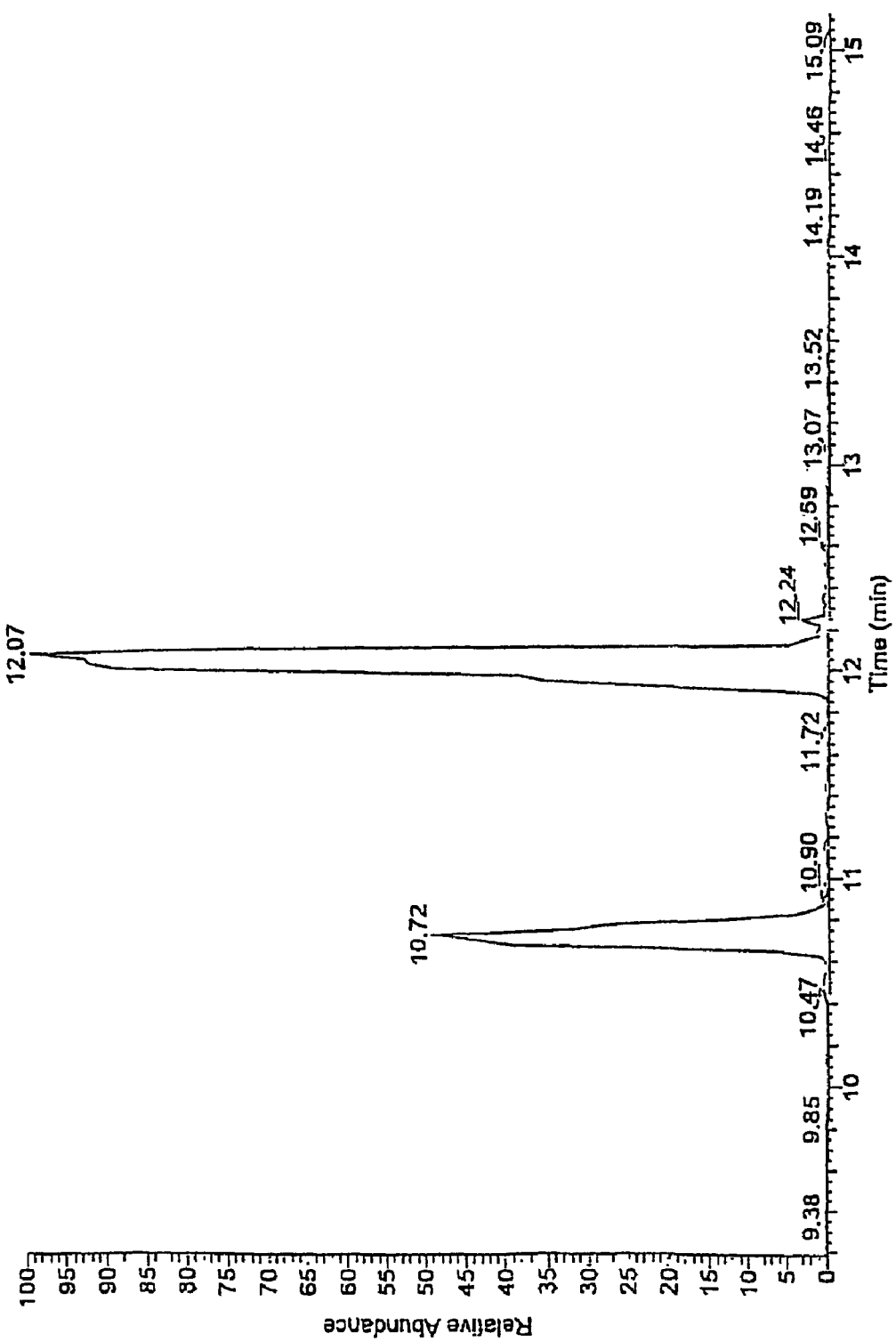
FIG. 4A shows LC analysis of photo-cleaved laminin B, with the addition of control phosphangiotensin at a concentration equivalent to the amount used in FIG. 2, (RT: 9.19-15.18, NL: 2.09E6 Base Peak m/z=560.0-570.0 MS 1hlight_0104 15121039).
Figure 4B:
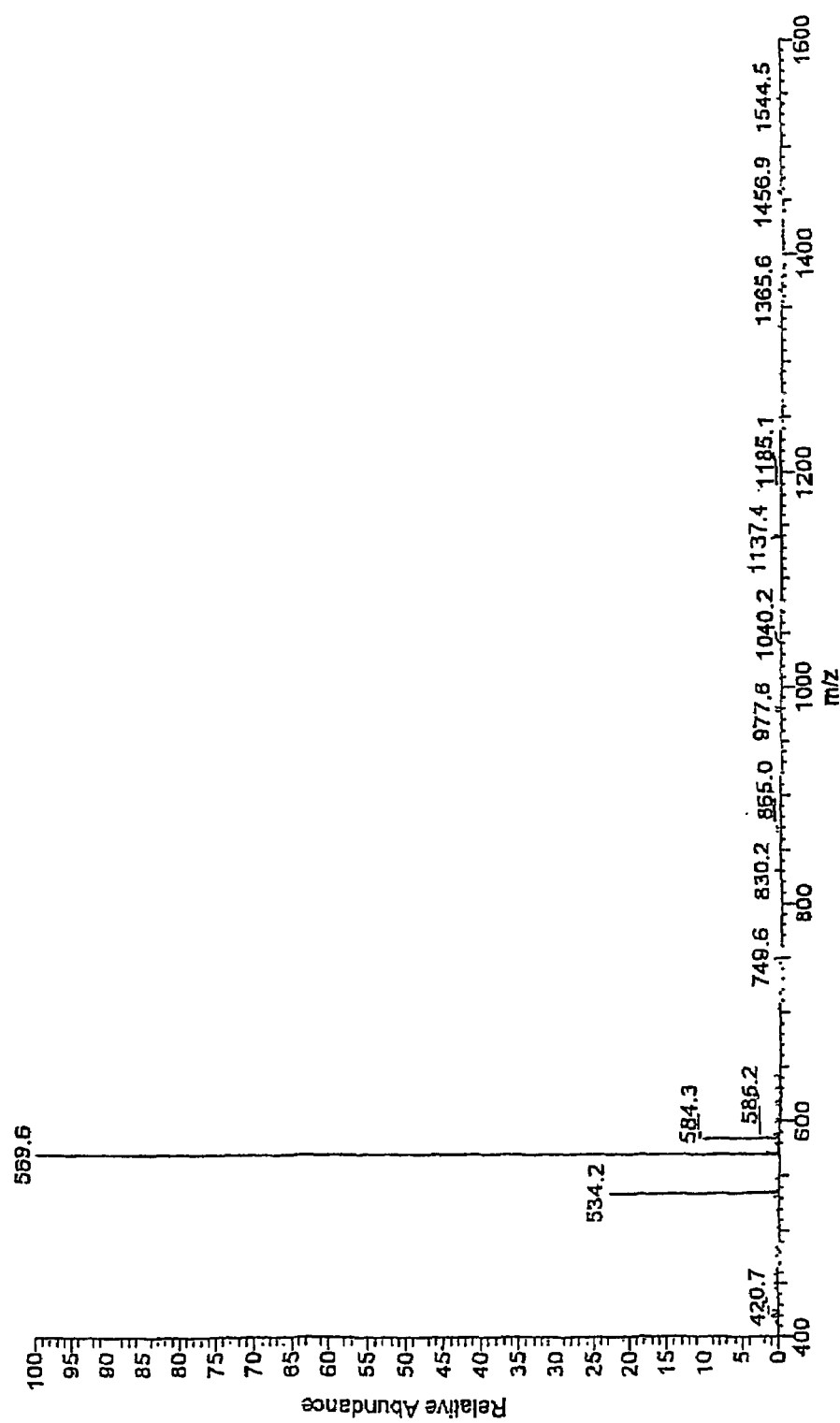
FIG. 4B shows MS analysis of the photo-cleaved laminin B peak eluting at 10.72 min in FIG. 4A, with the expected increase in mass due to modification, (1hlight_010415121039 #430, RT: 10.70, AV: 1, NL: 9.17E5, T: +c ESI Q3MS [400.00-1600.00]).

After washing the beads with 2M sodium chloride, methanol, and water, the beads were resuspended in buffer containing 0.2 M Tris, pH 8.0, 10 mM ethylenediaminetetraacetic acid (EDTA), again with the same concentration of phosphoangiotensin peptide spiked in as a control. The beads were exposed to 360 nm ultraviolet light for photocleavage. After photo-cleavage, the laminin B peptide with the expected mass modification (m/z=569 for [M+2H]2+ ion) was observed at a slightly slower elution time (10.72 min) compared to the initial laminin B peptide (FIG. 4). The longer retention time is consistent with the reduced polarity of the expected photo-cleaved product due to the addition of the transferred leucine amino acid. The structure of the photo-cleaved product was further confirmed by MS/MS sequencing analysis. The relative peak intensities of the modified laminin B peptide and phosphoangiotensin standard gave a rough estimate of the photo cleavage efficiency. At least 50 percent of the laminin B peptide originally input was recovered. The yield can be improved by further optimization of the capture and release reactions.

To illustrate the efficiency of the capture and release reactions, a mixture consisting of a cysteine-containing laminin B peptide and the non-cysteine-containing phosphoangiotensin was used. Laminin B was quantitatively captured onto the solid phase. After 1 h of photocleavage, the tagged laminin B was recovered; it showed the expected mass modification (+170 Da) due to the addition of leucine tag to the cysteine residue, which was also confirmed by MS/MS. The hydrophobic nature of the leucine tag increases the retention time of tagged laminin B as compared with the untagged form. The signal intensities of untagged and tagged laminin B, contrasting with the identical amounts of phosphoangiotensin, indicated specific capture and almost complete recovery of tagged laminin B. Longer photocleavage time did not affect either the yield or the quality of the tagged laminin B, indicating that photocatalyzed side reactions did not occur to any substantial extent.

These results demonstrate the successful transfer of the amino acid leucine to the sulfhydryl side chain of a peptide via capture-and release chemistry. These results exemplify a general approach to selectively capture peptides and transfer functional groups such as amino acids to the peptides.

EXAMPLE II

Modification of an Amino Group of a Polypeptide to Incorporate a Sulfydryl Group This example describes the N-terminal modification of a peptide to incorporate a sulfhydryl group.

Figure 5:
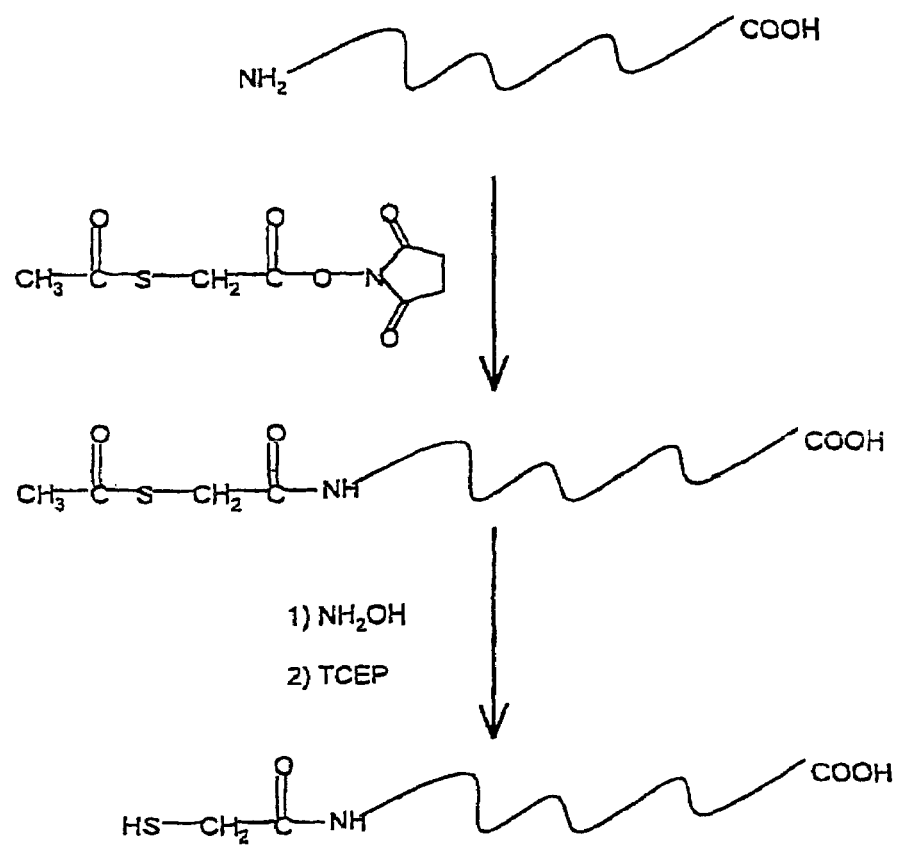
FIG. 5 shows a strategy for tagging of the primary amine groups of a polypeptide to incorporate a sulfhydryl group. The amino group(s) of a polypeptide is/are modified by N-succinimidyl S-acetylthioacctate (SATA). Upon hydroxylamine treatment, followed by reduction with tris(2-carboxyethyl)phosphine (TCEP), the amino group of the polypeptide is converted into a sulfhydryl group.

In cases in which peptides do not contain cysteine residues, the peptide can be modified to incorporate a sulfhydryl group, allowing conversion of an amino group to a sulfhydryl group and capture of the peptide via the incorporated sulfhydryl group. The strategy for modification of an amino group of a polypeptide is illustrated in FIG. 5.

Phosphoangiotensin was used to demonstrate the principle of modifying an amino group to a sulfhydryl group. The peptide was first modified by N-succinimidyl S-acetylthioacetate (SATA), which is reactive towards primary amine specifically. Phosphoangiotensin was modified as shown in FIG. 5. Briefly, phosphoangiotensin was incubated with 10 mM SATA for 30 min in 0.1 M $K_3PO_4$, pH 8.0, at room temperature.

Figure 6A:
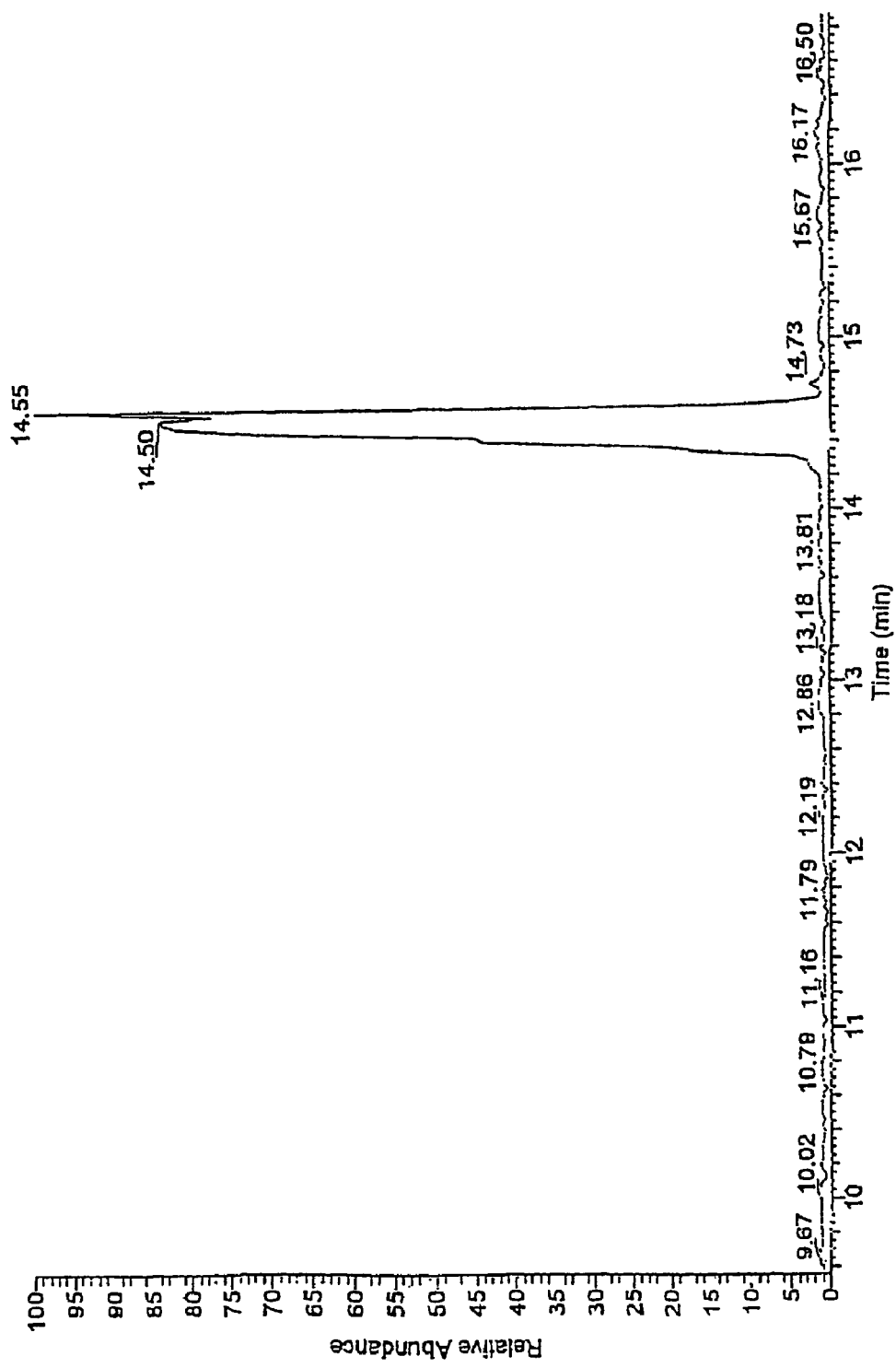
FIG. 6A shows LC analysis of SATA treated phosphoangiotensin, (RT: 9.56-16.88, NL: 3.29E7 Base Peak MS sata15min).
Figure 6B:
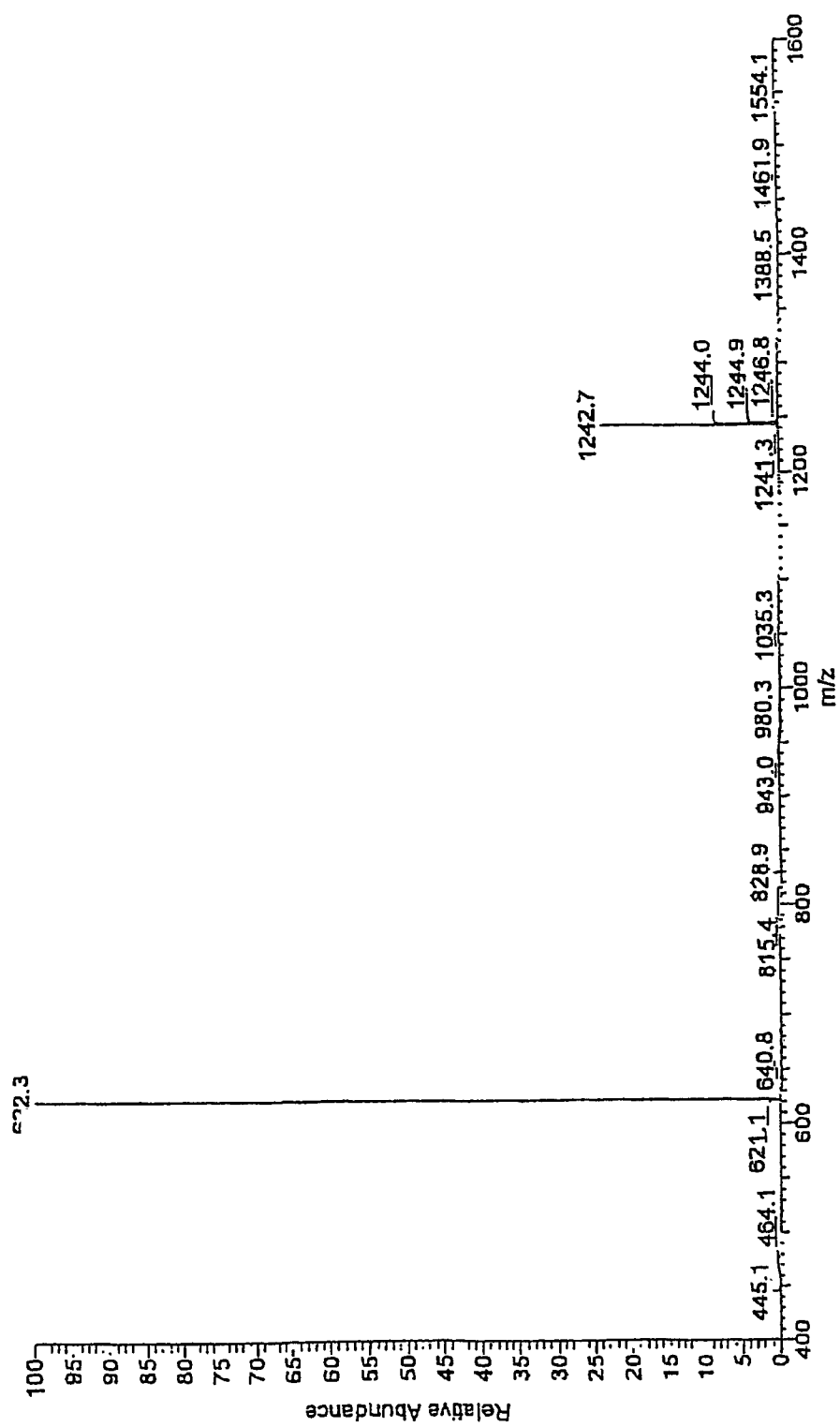
FIG. 6B shows MS analysis of the SATA treated phosphoangiotensin, (sata15min #582, RT: 14.48, AV:1, NL: 2.75E7, T: +c ESI Q3MS [400.00-1600.00]). The two main signals represent the singly charged, [M+H]+=1242.7 mass units, and doubly charged, [M+2H]2+=622.3 mass units, forms.

The modified phosphoangiotensin was analyzed by LC-MS. The N-terminal modification of the peptide was observed. The data shown in FIG. 6 indicate that a single product eluted at 14.5-14.55 min with m/z=622.3 for [M+2H]2+ions. The measured mass correlated well with the calculated mass for SATA derivatized phosphoangiotensin peptide (m/z=622.3).

Figure 7A:
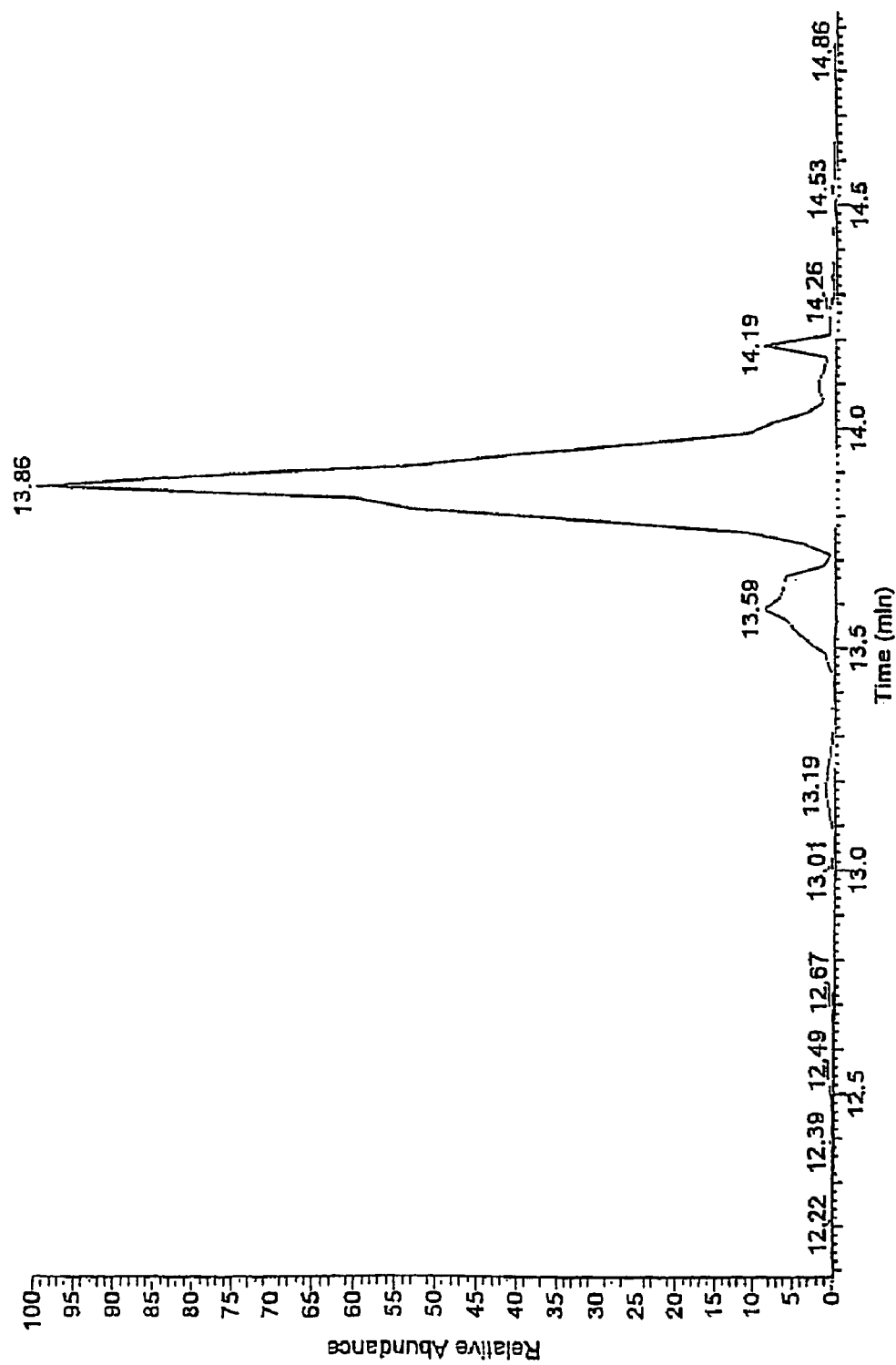
FIG. 7A shows LC analysis of the reduced modified phosphoangiotensin, (RT: 12.08-14.93, NL: 1.32E7 Base Peak MS 30min10m MTCEP).
Figure 7B:
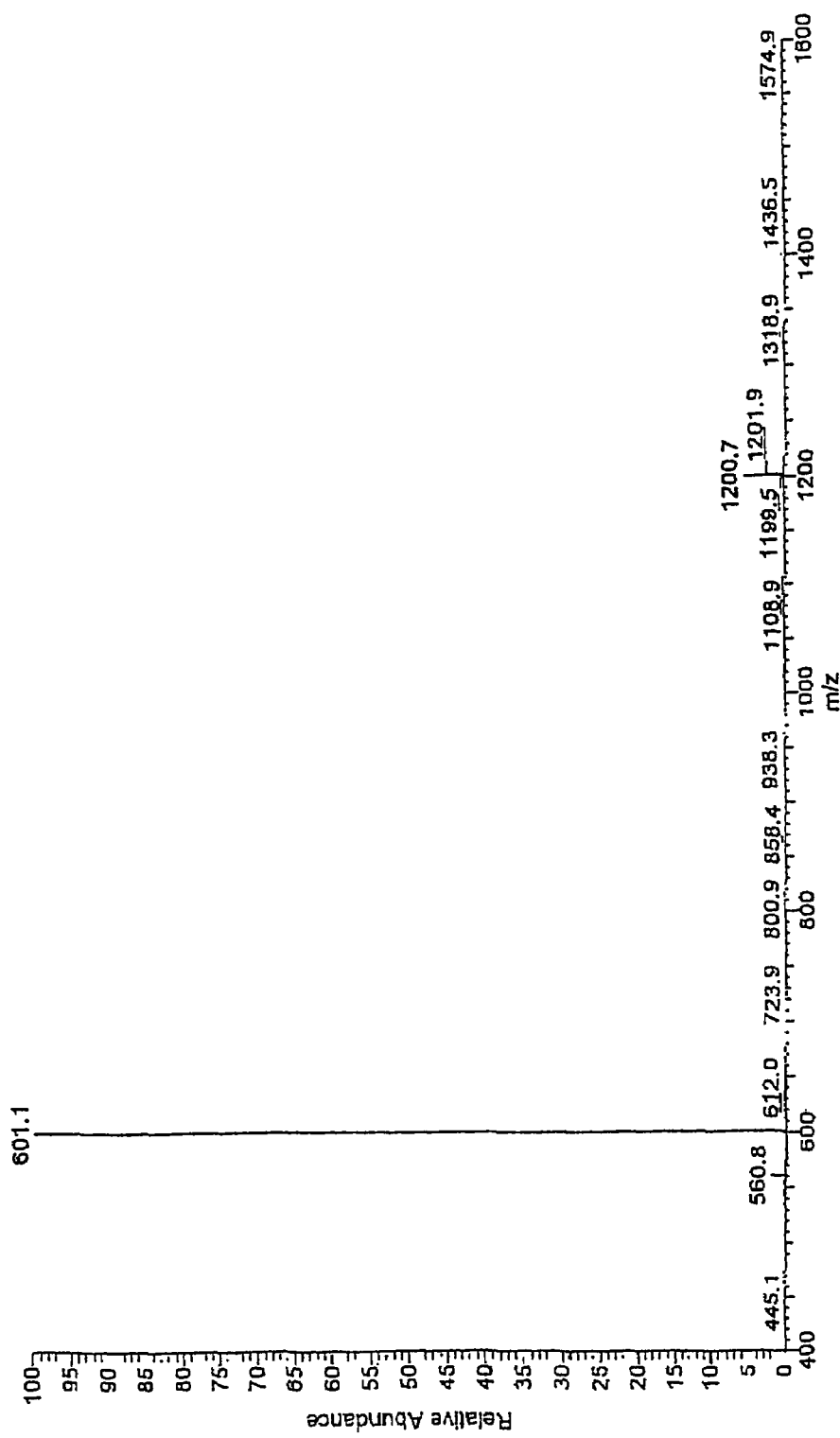
FIG. 7B shows MS analysis of the reduced modified phosphoangiotensin, indicating the expected change in mass due to the modification, (30min10mMTCEP #557 RT: 13.86, AV: 1, NL: 1.32E7, T: +c ESI Q3MS [400.00-1600.00]). The two main signals represent the singly charged, [M+H]+=1200.7 mass units, and doubly charged, [M+2H]2+=601.1 mass units, forms.

The modified peptide was treated with 0.1 M hydroxylamine at pH 8 for 2 hours, followed by reduction with 5 mM TCEP for 30 min. As indicated in FIG. 5, treatment by hydroxylamine and reduction by TCEP generate a free SH group in the SATA-derivatized phosphoangiotensin. Data from the LC-MS analysis of such a treated compound is shown in FIG. 7. Again, a single product eluting at 13.86 min was observed. MS analysis indicated m/z=601 for [M+2H]2+ions. The measured mass agreed with the calculated mass for the expected peptide product (m/z=601). Thus, conversion of amino groups of peptides into free SH groups can be made quantitatively with a minimal amount of side products. Furthermore, such a sulfhydryl modified polypeptide can be subsequently captured as described in Example I.

These results demonstrate that an amino group of a polypeptide can be essentially quantitatively modified to incorporate a sulfhydryl group.

EXAMPLE III

Analysis of Protein Samples by Incorporation of Heavy and Light Labels

This example describes differential labeling of two samples for qualitative and quantitative analysis of sample polypeptides by mass spectrometry.

Figure 8:
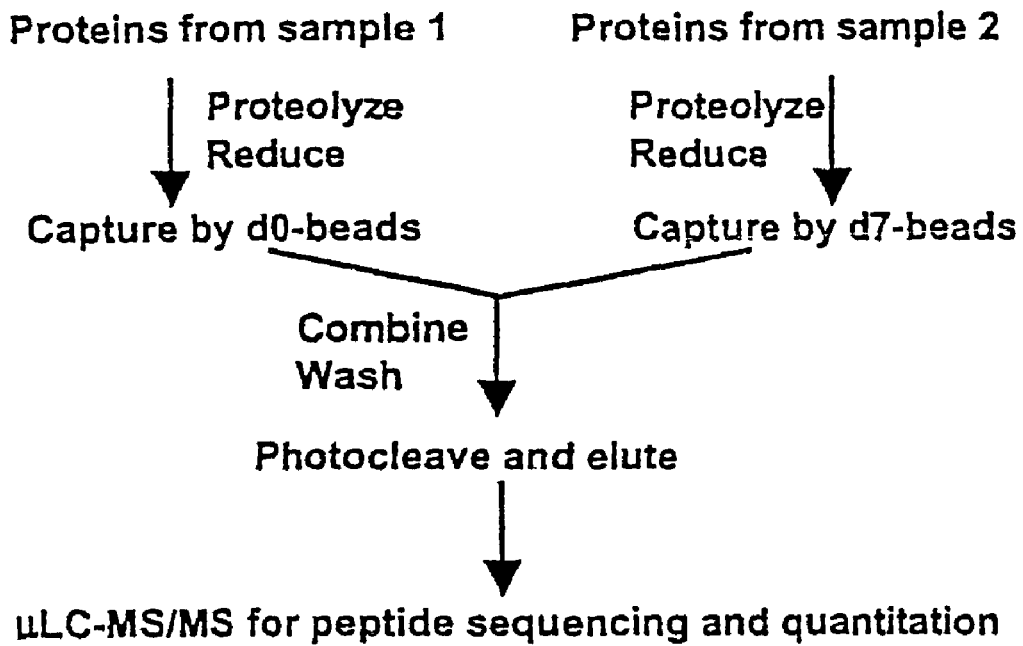
FIG. 8 shows a schematic outline for comparison of two samples by differential modification using a solid phase capture. Two protein samples to be compared are subjected to proteolysis, for example, with trypsin. In the case of a sulfhydryl reactive reagent, Cys-containing peptides are reduced and captured by beads carrying differentially isotopically labeled reagents, for example, d0-leucine or d7-leucine tag containing 0 or 7 deuteriums, respectively. The beads are combined and washed, and tagged peptides are released by photocleavage. The released peptides can be further characterized, for example, using mass spectrometry (MS) such as microcapillary liquid chromatography and tandem mass spectrometry (μLC-MS/MS).

A schematic diagram of the differential labeling of polypeptides is shown in FIG. 8. The samples are digested with a protease such as trypsin. The digested polypeptides are treated as described in Example I. If desired, the sample polypeptides can be modified by the method described in Example II to examine polypeptides lacking cysteine.

One digested sample is added to beads covalently attached to a chemical group containing a non-deuterated amino acid such as leucine or another suitable amino acid. The second sample is added to beads covalently attached to a chemically identical group except that the chemical group contains a deuterated form of the same amino acid. The differentially isotopically labeled leucine differs in mass by 7 or 10 mass units, depending on the state of deuteration of leucine.

After covalently coupling the sample polypeptides to the respective beads containing differentially isotopically labeled amino acids, the beads are combined and then cleaved by photo-cleavage. The photo-cleaved polypeptides, now differentially labeled, are analyzed simultaneously by mass spectrometry. MS can be used for quantitation of the samples by direct comparison of the intensities of MS signals from the two samples, which differ by a predetermined mass and can be readily distinguished on MS as doublet peaks differing by the predetermined mass. In addition, the samples can be sequenced by MS.

This example demonstrates differential labeling and analysis of sample molecules by mass spectrometry.

EXAMPLE IV

Modification of Captured Phosphopeptides

This example describes the capture of polypeptides and modification of captured phosphopeptides.

Polypeptides from a sample are captured on beads essentially as described in Example I. The captured polypeptides are modified essentially as described in Zhou et al., *Nature Biotechnol.* 19:375-378 (2001), which is incorporated herein by reference.

Briefly, the captured polypeptides are modified by the following steps. (1) Amino protection: peptide amino groups are optionally protected using t-butyl-dicarbonate (tBoc) chemistry to eliminate the potential for intra- and intermolecular condensation in subsequent reactions. (2) Condensation reaction: carbodiimide catalyzes condensation reactions between the peptides and excess amine to form amide and phosphoramidate bonds at the carboxylate and phosphate bonds of the peptides, respectively. (3) Phosphate regeneration: free phosphate groups are regenerated by brief acid hydrolysis of the phosphoramidate bonds. (4) Condensation and reduction: a carbodiimide-catalyzed condensation reaction attaches a cystamine to the regenerated phosphate group(s). Reduction of the internal disulfide of cystamine next generates a free sulfhydryl group for every phosphate of the captured phosphopeptides. (5) Release of modified polypeptides: the captured polypeptides are released from the solid support by cleavage of the chemical cleavage group, for example, using light as described in Example I. (6) Solid-phase capture: the released polypeptides, including the modified phosphopeptides containing a free sulfhydryl, are attached to a second solid phase by reacting the free sulfhydryl groups in the peptides with iodoacetyl groups immobilized on glass beads. (7) Phosphopeptide recovery: following stringent washing of the resin, phosphopeptides are recovered by cleavage of phosphoramidate bonds using trifluoracetic acid (TFA) at a concentration that also removes the tBoc protection group, thus regenerating peptides with free amino and phosphate groups. The carboxylate groups remain blocked from step (2).

The chemical reactions are carried out as described below in more detail. The solid phase containing captured polypeptides is incubated in 50% (vol/vol) of 0.1 M phosphate buffer, pH 11, and acetonitrile. 0.1 M tBoc is added for 4 h at room temperature. Acetonitrile is then removed. The solid phase containing captured polypeptides is incubated in 1M ethanolamine, 25 mM N-hydroxysuccinimide (NHS), and 0.5 M of N,N'-dimethylaminopropyl ethyl carbodiimide HCL (EDC) and incubated for 2 h at room temperature. 10% TFA is added and incubated 30 min at room temperature. The solid phase is washed to remove excess reagents and to desalt, and 1 M imidazole, pH 6.0, is added. 0.5 M EDC is added for 3 hours at room temperature. The solid phase is washed and then incubated with 1M cystamine, pH 8.0, for 2 h at 50° C. The solid phase is washed with water and then reduced with 10 mM dithiothreitol (DTT) to generate free sulfhydryl groups. The solid phase is washed to remove DTT, and then the captured molecules are released by cleavage of the cleavable functional group.

The released polypeptides, including the phosphopeptides modified with sulfhydryl groups, are incubated for at least 2 h with a second type of solid phase beads, which have iodoacetyl groups and are titrated to pH 8.0 with 1 M Tris, pH 8.0, 50 mM ethylenediamine tetraacetic acid (EDTA). Beads with immobilizede iodoacetyl gropus are prepared by a 2 h reaction between 3 equivalents of iodoacetic anhydride and 1 equivalent of amino beads (G4643; Sigma; St. Louis Mo.) with 3.3 equivalents of diisopropylethylamine in dimethylformide. Since a tyrosine adduct with carbodiimide is a possible side reaction, the captured phosphopeptides modified with sulfhydryl groups are incubated in 1 M hydroxylamine, pH 10, for 2 h at room temperature to restore any modified tyrosines. The beads are then washed sequentially with 2 M NaCl, methanol and water to remove nonspecifically bound molecules. The beads are incubated with 100% TFA for 30 min to recover phosphopeptides and concurrently remove tBoc protection from tBoc modified groups. The recovered phosphopeptides are then analyzed, for example, by mass spectrometry.

The molecules captured on the first solid support are generally released just prior to re-capture on the second solid phase, which selectively captures the modified phosphopeptides, allowing efficient washing and removal of chemicals used to modify the captured polypeptides. However, the peptides can be released at an earlier stage, even after the initial capture, if binding to the first solid phase is intended only to transfer a label or tag to the captured polypeptides. Alternatively, the modification of phosphopeptides can be carried out essentially as described in Zhou et al., and then the recovered phosphopeptides captured and labeled essentially as described in Example I.

This example demonstrates the selective modification and isolation of phosphopeptides.

EXAMPLE V

Isolation and Isotopic Labeling of Yeast Proteins

This example describes a method for the site-specific, stable isotopic labeling of cysteinyl peptides in complex peptide mixtures through a solid-phase capture and release process, and the concomitant isolation of the labeled peptides.

Yeast proteins were differentially isotopically labeled by capture and release from the solid-phase isotope tagging reagent. The recovered peptides were analyzed by microcapillary liquid chromatography and tandem mass spectrometry (μLC-MS/MS) to determine their sequences and relative quantities. The method was used to detect galactose-induced changes in protein abundance in the yeast *Saccharomyces cerevisiae*. A side-by-side comparison with the isotope-coded affinity tag (ICAT) method (Gygi et al., supra, 1999) demonstrated that the solid-phase method for stable isotope tagging of peptides is comparatively simpler, more efficient, and more sensitive.

Cysteinyl peptides from two samples to be compared were covalently captured on the solid phase containing isotopically heavy or normal tag. The beads were then combined, washed, and exposed to UV light (360 nm, chosen to minimize any possible photocatalyzed side reactions). This resulted in photocleavage of the linker and the transfer of isotope tags from the solid phase onto the side chain of cysteine residues. Finally, recovered tagged peptides were analyzed by μLC-MS/MS to determine the sequence and relative abundance of each peptide, essentially as described previously (Gygi et al., supra, 1999).

Stable isotope tagging is a general strategy for quantitative analysis of proteins by mass spectrometry (Gygi et al., supra, 1999; Oda et al., *Proc. Natl. Acad. Sci. USA* 96:6591-6596 (1999); Ideker et al., *Science* 292:929-934 (2001); Han et al., *Nat. Biotechnol.* 19:946-951 (2001)). To compare the performance of the solid-phase approach with that of the standard ICAT approach (Gygi et al., supra, 1999), a side-by-side comparison was performed in which the two methods were used to detect protein expression changes in the yeast *S. cerevisiae* in response to induction with galactose. Two different amounts of starting protein material were evaluated, 100 μg for large sample load and 10 μg for small sample load of the same yeast proteins. Because the objective was to compare the relative performance of the labeling strategies, and not the peptide separation or protein identification strategies, single LC-MS/MS runs were performed on all samples for protein identification. This minimized variations in the results due to sample processing rather than labeling, but probably resulted in the identification of fewer proteins than would be obtainable with larger sample sizes and optimized peptide separations upstream of LC-MS/MS.

For preparation of yeast protein samples, yeast strain BY4742 was grown in either 100 ml YPR (1% yeast extract, 2% peptone (Difco, Detroit, Mich.), and 2% raffinose) or YPR+2% galactose to an $A_{600}$ of 1. Spheroplasts were prepared as described previously (Ausubel et al., supra). Spheroplasts were lysed in 50 mM Tris (pH 8.0), 5 mM EDTA, 6 M urea, 0.5% SDS. Cell lysate was centrifuged at 15,000 g (14,000 rpm) for 15 min. The supernatant was collected and desalted on an Econo-Pac 10DG column (Bio-Rad, Hercules, Calif.) in 50 mM Tris (pH 8.0), 5 mM EDTA. Protein concentration was determined by Bio-Rad protein assay.

For isolation and isotope labeling of tryptic digest of yeast proteins by the solid-phase capture-release method, large and small scale experiments were performed. For the larger-scale experiment, 50 μg of each protein extract (100 μg combined) from yeast cells grown with or without galactose was prepared in 100 μl of 200 mM Tris (pH 8.0), 5 mM EDTA. Each protein extract was digested by 5 μg trypsin for 3 h at 37° C. and reduced with 5 mM TCEP, and cysteinyl peptides were then captured by beads with either d0- or d7-leucine tag for 15 min as described in Example I. The beads were combined and washed, and labeled peptides were released by 2 h of light illumination. The released peptides were loaded on an MCX column (Waters, Milford, Mass.) and washed sequentially with 4 ml 0.1% trifluoroacetic acid (TFA), 4 ml 80% acetonitrile/0.1% TFA, and water (to neutralize). Peptides were eluted by 1 ml of a mixture of 9 volumes methanol and 1 volume 28% ammonia, and dried under reduced pressure. Dried peptides were resuspended in water for μLC-MS/MS analysis. Next, 20% of the recovered peptides (representing 20 μg of combined proteins) were analyzed by μLC-MS/MS using a LCQ ion-trap mass spectrometer (Finnigan, San Jose, Calif.) as described previously (Zhou et al., Nat. Biotechnol. 19:375-378 (2001). Protein identification and quantification were performed with Sequest and existing software (Han et al., Nat. Biotechnol. 19:946-951 (2001); Eng et al., J. Am. Soc. Mass Spectrom. 5:976-989 (1994)). For the small-scale experiment, 5 μg of each protein extract from cells grown with or without galactose was digested by 0.5 μg trypsin and processed as described above, and then 50% of the peptide mixture recovered (representing 5 μg of combined protein extracts) was analyzed by the same μLC-MS/MS method.

For isotope labeling of yeast proteins and isolation of peptides by ICAT, 100 μg of each protein extract from cells grown with or without galactose was prepared as starting material in labeling buffer containing 200 mM Tris (pH 8), 0.5 mM EDTA, 6 M urea, and 0.05% SDS. Proteins were reduced with 5 mM TCEP for 30 min, and 100 μg of d0- or d8-ICAT was added to the protein extracts from raffinose- or galactose-grown cells, respectively. After 90 min of labeling at room temperature, the reactions were quenched by addition of β-mercaptoethanol to 10 mM and combined. Each sample was diluted 10-fold with 20 mM Tris (pH 8.3), 0.01% SDS. Trypsin (10 μg) was added to digest proteins for 3 h at 37° C. The sample was diluted with an equal volume of buffer A (5 mM $KH_2PO_4$ (pH 3), 25% $CH_3CN$) and the pH was adjusted to 3 with dilute TFA. Either 100 μg (large-scale experiment) or 10 μg (small-scale experiment) of the combined protein digest was applied to a cation-exchange cartridge (Applied Biosystems, Foster City, Calif.) equilibrated in buffer A. The cartridge was washed with 2 ml buffer A, followed by 2 ml of buffer A+40 mM KCl. Bound peptides were eluted with 600 μl buffer A+600 mM KCl. Sample volume was reduced to 300 μl under reduced pressure, and 500 μl 2×PBS and 12 μl 1 M $NH_4HCO_3$ were added. Samples were passed over a monomeric avidin cartridge (Applied Biosystems) and washed with 2 ml 2×PBS, 1 ml 1×PBS, and 1 ml 50 mM $NH_4HCO_3$ with 20% methanol. Labeled peptides were eluted with 1 ml 0.4% TFA with 30% acetonitrile, dried under reduced pressure, and resuspended in 10 μl of 0.4% acetic acid with 5% acetonitrile. For either the large- or small-scale experiment, the same amount of sample was analyzed by the same μLC-MS/MS method as used in the solid-phase method.

Figure 9:
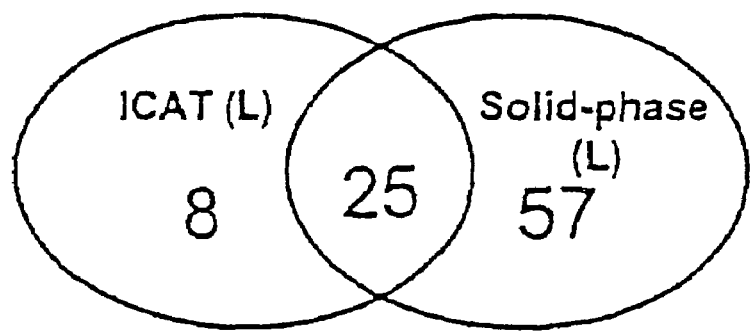
FIG. 9 shows a summary of the number of proteins identified and quantified by the solid-phase and ICAT methods.
Figure 9:
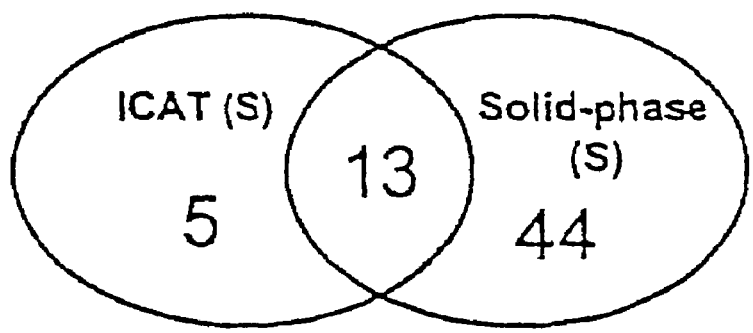
Figure 9:
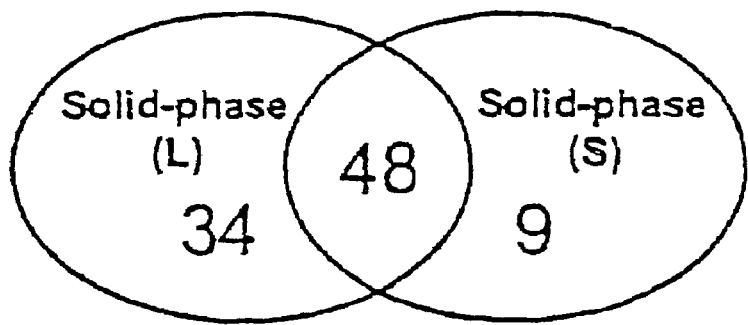

In both the small- and large-scale experiments, the number of proteins identified and quantified by the solid-phase method was greater than by ICAT (FIG. 9). Indeed, the solid-phase approach was more sensitive, identifying the majority of the proteins identified by conventional ICAT in addition to many others not identified by ICAT (FIG. 9A, 9B). Quantification of the same proteins identified in multiple experiments was also consistent. Thus, protein quantification was not influenced by either the structure of the isotope tag or the capture and release chemistry of the solid-phase method.

Galactose is known to strongly induce expression of several genes involved in galactose utilization, including galactokinase (GAL1), galactose permease (GAL2), galactotransferase (GAL7), and UDP-glucose-4-epimerase (GALX) (Johnston and Carlson, The Molecular and Cellular Biology of the Yeast Saccharomyces, Jones et al., eds., pp. 193-281, Cold Spring Harbor Press, Cold Spring Harbor, N.Y. (1992)). After induction with galactose, multiple peptides from proteins including GAL1, GAL2, GAL7, and GALX were identified and quantified by the solid-phase method. In contrast, using the ICAT method, only one peptide from the GAL1 protein was identified in both the small- and large-sample-load experiments, and a lower signal-to-noise ratio than with the solid-phase method was found. These data confirmed the superior sample recovery and sensitivity of the solid-phase over the ICAT approach. In addition, the reproducibility of the solid-phase method was demonstrated by the substantial overlap in proteins identified by the small- and large-scale experiments (FIG. 9C).

These results show that the solid-phase method is simple, reproducible, efficient, and sensitive for quantitative protein analysis. Indeed, as compared with the ICAT method, it has several advantages. First, both the isolation of cysteine-containing peptides and the stable incorporation of isotopes are achieved essentially in a single step. Thus, the solid-phase method is faster and simpler, requiring less manual input than the ICAT approach. Second, the covalent capture of peptides to a solid phase permits the use of stringent wash conditions to remove non-covalently associated molecules. Indeed, the experiments presented here resulted in the recovery of almost exclusively cysteinyl peptides. Third, this procedure is unaffected by the presence of proteolytic enzymes such as trypsin or of strong denaturants and detergents such as urea and SDS. There is therefore no need for additional steps to remove such molecules. Because of the minimal sample handling, this solid-phase method is more sensitive than the ICAT method. As many biologically interesting events involve relatively low-abundance regulatory proteins, the solid-phase method is useful for the analysis of induced changes to such proteins. Fourth, the standard solid-phase peptide chemistry involved in the coupling process allows the use of a range of natural or unnatural amino acids as the isotopic mass tag in place of the d0/d7-leucine used here. This can facilitate the synthesis of beads with a range of mass tags for analysis of multiple samples (more than two) in a single experiment. Fifth, the mass tag on the cysteine used here weighs 170 Da for the d0-leucine tag. Because of the small size and the chemical nature of the tag, the observed peptide fragmentation in the MS/MS mode was not complicated by undesirable fragmentation of the label itself, in contrast to the situation with ICAT-labeled peptides (Han et al., supra, 2001). Finally, before photocleavage, the covalently immobilized peptides provide ideal substrates for additional chemical and enzymatic reactions, if desired (Zhou et al., supra, 2001).

One significant way that the solid-phase method differs from the ICAT method is that the solid-phase reagent labels peptides after proteolysis, whereas in ICAT, proteins are labeled before proteolysis. Therefore, the ICAT approach is preferred in cases where separation of labeled proteins is required, such as gel electrophoresis. The solid-phase method described above provides a tool suitable for general application to quantitative proteomics and is amenable to automated implementation. It thus represents a step forward towards much wider applications of stable isotope tagging for quantitative protein analysis by mass spectrometry.

These results demonstrate differential isotopic labeling of complex protein mixtures suitable for quantitative proteome analysis.

Throughout this application various publications have been referenced. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A method for labeling a sample molecule, comprising:
   (a) contacting a sample molecule with a composition comprising a solid support coupled to a chemical group comprising a cleavable functional group, a tag and a reactive group, wherein said cleavable functional group is covalently coupled to said solid support, said tag is covalently coupled to said cleavable functional group, and said reactive group is covalently coupled to said tag and wherein said cleavable functional group, said tag and said reactive group are positioned relative to each other to allow transfer of said tag to said sample molecule and release of said sample molecule from said solid support upon cleavage of said cleavable functional group, under conditions allowing said sample molecule to covalently bind to said reactive group, thereby covalently linking said sample molecule to said solid support; and
   (b) cleaving said cleavable functional group, thereby transferring said tag to said sample molecule and releasing said tagged sample molecule from said solid support, thereby labeling said sample molecule with said tag.

2. The method of claim 1, wherein said sample molecule is selected from the group consisting of a polypeptide, a nucleic acid, a lipid, a second messenger, and a metabolite.

3. The method of claim 1, wherein said sample molecule is a polypeptide.

4. The method of claim 3, wherein said polypeptide has a modification selected from the group consisting of phosphorylation, glycosylation, ubiquitination, acetylation, prenylation, palmitylation, myristylation, sulfation, and hydroxylation.

5. The method of claim 4, wherein said polypeptide is a phosphopolypeptide.

6. The method of claim 1, wherein said solid support is a glass bead.

7. The method of claim 1, wherein said cleavable functional group is a chemical linker cleavable by light, an acid, a base or an enzyme.

8. The method of claim 1, wherein said tag is a mass spectrometry tag.

9. The method of claim 1, wherein said tag is selected from the group consisting of a stable isotope tag, an isotope distribution tag, and a charged amino acid.

10. The method of claim 9, wherein said tag is a stable isotope coded amino acid.

11. The method of claim 10, wherein said tag is a deuterated or non-deuterated amino acid.

12. The method of claim 8, wherein one of said functional groups comprises an element having a characteristic isotope distribution.

13. The method of claim 3, wherein said reactive group of said chemical group is selected from the group consisting of a succinimide ester group and an iodoacetyl group.

14. The method of claim 3, wherein a primary amine group of said polypeptide is modified by treatment with N-succinimidyl S-acetylthioacetate, hydroxylamine, and tris (2-carboxyethyl)phosphine.

15. The method of claim 4, wherein said polypeptide is isolated prior to contacting said solid support, wherein said polypeptide is isolated using an antibody having specific binding activity to said modification of said polypeptide.

16. The method of claim 1, wherein the method steps are performed by an automated process.

17. The method of claim 1, wherein at least 50 percent of said sample molecule contacted with said solid support is released.

18. The method of claim 8, further comprising analyzing said released sample molecule using mass spectrometry.

19. A method for labeling a sample molecule, comprising:
   (a) contacting a sample molecule with a composition having the structure

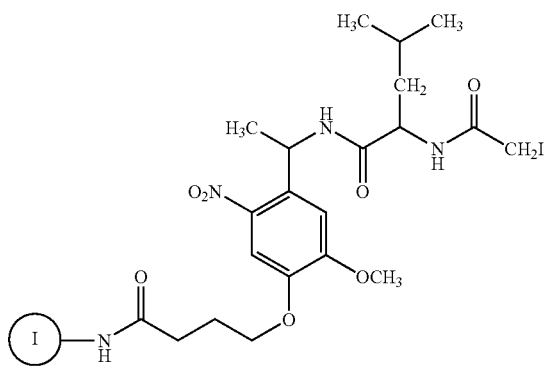

wherein (1) represents a solid support and wherein the leucyl group of said structure contains an isotope tag, under conditions allowing said sample molecule to covalently bind to the I reactive group and react with a sulfhydryl group of said sample molecule, thereby covalently linking said sample molecule to said solid support; and
   (b) cleaving the cleavable functional group of said structure, thereby transferring said leucyl group containing said isotope tag to said sample molecule and releasing said tagged sample molecule from said solid support, thereby labeling said sample molecule with said isotope tag.

20. The method of claim 19, wherein said sample molecule is selected from the group consisting of a polypeptide, a nucleic acid, a lipid, a second messenger, and a metabolite.

21. The method of claim 19, wherein said sample molecule is a polypeptide.

22. The method of claim 21, wherein said polypeptide has a modification selected from the group consisting of phosphorylation, glycosylation, ubiquitination, acetylation, prenylation, palmitylation, myristylation, sulfation, and hydroxylation.

23. The method of claim 22, wherein said polypeptide is a phosphopolypeptide.

24. The method of claim 19, wherein said solid support is a glass bead.

25. The method of claim 19, wherein said leucyl group contains deuterium.

26. The method of claim 19, wherein said leucyl group contains $^{13}C$.

27. The method of claim 21, wherein a primary amine group of said polypeptide is modified by treatment with N-succinimidyl S-acetylthioacetate, hydroxylamine, and tris (2-carboxyethyl)phosphine.

28. The method of claim 22, wherein said polypeptide is isolated prior to contacting said solid support, wherein said polypeptide is isolated using an antibody having specific binding activity to said modification of said polypeptide.

29. The method of claim 19, wherein the method steps are performed by an automated process.

30. The method of claim 19, wherein at least 50 percent of said sample molecule contacted with said solid support is released.

31. The method of claim 19, further comprising analyzing said released sample molecule using mass spectrometry.

* * * * *